US009617274B1

(12) United States Patent
Moriarty et al.

(10) Patent No.: US 9,617,274 B1
(45) Date of Patent: Apr. 11, 2017

(54) SYNTHETIC NORIBOGAINE

(71) Applicant: DemeRx, Inc., Fort Lauderdale, FL (US)

(72) Inventors: Robert M. Moriarty, Michiana Shores, IN (US); Richard D. Gless, Jr., Oakland, CA (US)

(73) Assignee: DEMERX, INC., Fort Lauderdale, FL (US)

( * ) Notice: Subject to any disclaimer, the term of this patent is extended or adjusted under 35 U.S.C. 154(b) by 0 days.

(21) Appl. No.: 14/636,080

(22) Filed: Mar. 2, 2015

Related U.S. Application Data

(63) Continuation of application No. 13/593,454, filed on Aug. 23, 2012, now abandoned.

(60) Provisional application No. 61/528,070, filed on Aug. 26, 2011.

(51) Int. Cl.
*A61K 31/55* (2006.01)
*C07D 487/22* (2006.01)

(52) U.S. Cl.
CPC ............ *C07D 487/22* (2013.01); *A61K 31/55* (2013.01)

(58) Field of Classification Search
CPC ...................................................... A61K 31/55
See application file for complete search history.

(56) References Cited

U.S. PATENT DOCUMENTS

| 2,813,873 | A | | 11/1957 | Janot et al. |
|---|---|---|---|---|
| 2,877,229 | A | * | 3/1959 | Taylor .................. C07D 487/04 540/579 |
| 3,516,989 | A | | 6/1970 | Sallay |
| 3,557,126 | A | | 1/1971 | Sallay |
| 3,574,220 | A | | 4/1971 | Sallay |
| 3,639,408 | A | | 2/1972 | Nagata et al. |
| 3,715,361 | A | | 2/1973 | Epstein et al. |
| 3,716,528 | A | | 2/1973 | Nagata et al. |
| 3,875,011 | A | | 4/1975 | Rubenstein et al. |
| 4,107,288 | A | | 8/1978 | Oppenheim et al. |
| 4,272,541 | A | | 6/1981 | Kotick et al. |
| 4,375,414 | A | | 3/1983 | Strahilevitz |
| 4,422,955 | A | | 12/1983 | Bryant |
| 4,444,758 | A | | 4/1984 | Scherschlicht et al. |
| 4,462,941 | A | | 7/1984 | Lee et al. |
| 4,464,378 | A | | 8/1984 | Hussain |
| 4,499,096 | A | | 2/1985 | Lotsof |
| 4,573,995 | A | | 3/1986 | Chen et al. |
| 4,587,243 | A | | 5/1986 | Lotsof |
| 4,604,365 | A | | 8/1986 | O'Neill et al. |
| 4,620,977 | A | | 11/1986 | Strahilevitz |
| 4,626,539 | A | | 12/1986 | Aungst et al. |
| 4,661,492 | A | | 4/1987 | Lewis et al. |
| 4,668,232 | A | | 5/1987 | Cordes et al. |
| 4,737,586 | A | | 4/1988 | Potier et al. |
| 4,806,341 | A | | 2/1989 | Chien et al. |
| 4,857,523 | A | | 8/1989 | Lotsof |
| 4,904,768 | A | | 2/1990 | Saulnier et al. |
| 5,026,697 | A | | 6/1991 | Lotsof |
| 5,075,341 | A | | 12/1991 | Mendelson et al. |
| 5,145,684 | A | | 9/1992 | Liversidge et al. |
| 5,149,538 | A | | 9/1992 | Granger et al. |
| 5,152,994 | A | | 10/1992 | Lotsof |
| 5,283,247 | A | | 2/1994 | Dwivedi et al. |
| 5,290,784 | A | | 3/1994 | Qu et al. |
| 5,316,759 | A | | 5/1994 | Rose et al. |
| 5,382,657 | A | | 1/1995 | Karasiewicz et al. |
| 5,426,112 | A | | 6/1995 | Zagon et al. |
| 5,552,406 | A | | 9/1996 | Mendelson et al. |
| 5,574,052 | A | | 11/1996 | Rose et al. |
| 5,578,645 | A | | 11/1996 | Askanazi et al. |
| 5,580,876 | A | | 12/1996 | Crain et al. |
| 5,591,738 | A | | 1/1997 | Lotsof |
| 5,616,575 | A | | 4/1997 | Efange et al. |
| 5,618,555 | A | | 4/1997 | Tokuda et al. |
| 5,703,101 | A | | 12/1997 | Rose et al. |
| 5,726,190 | A | | 3/1998 | Rose et al. |
| 5,760,044 | A | | 6/1998 | Archer |
| 5,861,422 | A | | 1/1999 | Rose et al. |
| 5,865,444 | A | | 2/1999 | Kempf et al. |
| 5,925,634 | A | | 7/1999 | Olney |
| 5,935,975 | A | | 8/1999 | Rose et al. |
| 6,211,360 | B1 | | 4/2001 | Glick et al. |
| 6,291,675 | B1 | | 9/2001 | Coop et al. |
| 6,348,456 | B1 | | 2/2002 | Mash et al. |
| 6,451,806 | B2 | | 9/2002 | Farrar |
| 6,806,291 | B1 | | 10/2004 | Sunkel et al. |
| 6,864,271 | B2 | | 3/2005 | Bazan et al. |
| 7,220,737 | B1 | | 5/2007 | Mash |
| 7,737,169 | B2 | | 6/2010 | Corrie et al. |

(Continued)

FOREIGN PATENT DOCUMENTS

| CA | 2039197 | 9/1995 |
|---|---|---|
| DE | 22 17 132 | 10/1972 |

(Continued)

OTHER PUBLICATIONS

"A Mild Deprotection Strategy for Allyl-Protecting Groups and Its Implications in Sequence Specific Dendrimer Synthesis" by Vutukuri et al., J. Org. Chem. 68, 1146-49 (2003).*
Buchi et al., "Chemical Transformations of Ibogaine," Journal of the American Chemical Society, 88:11, Jun. 5, 1966, pp. 2532-2535.
Extended European Search Report on EP Application 13740942.1, mailed Sep. 10, 2015.
JD Roberts, "Separation and Purification. Identification of Organic Compounds by Spectroscopic Techniques," Chapter 9, 1977 pp. 257-349.
Office Action on Chinese Application 201110083808.7, mailed Jul. 15, 2015 English translation provided.

(Continued)

*Primary Examiner* — Theodore R West
(74) *Attorney, Agent, or Firm* — Foley & Lardner LLP

(57) ABSTRACT

Synthetic noribogaine preferably free of ibogaine and, optionally, one or more of other naturally occurring *Tabernanth iboga* alkaloids, is provided.

10 Claims, No Drawings

(56) References Cited

U.S. PATENT DOCUMENTS

| | | | |
|---|---|---|---|
| 7,745,479 | B2 | 6/2010 | Nettekoven et al. |
| 7,754,710 | B2 | 7/2010 | Mash |
| 8,017,151 | B2 | 9/2011 | Batrakova et al. |
| 8,178,524 | B2 | 5/2012 | Mash |
| 8,362,007 | B1 | 1/2013 | Mash et al. |
| 8,637,648 | B1 | 1/2014 | Mash et al. |
| 8,741,891 | B1 | 6/2014 | Mash |
| 8,765,737 | B1 | 7/2014 | Mash et al. |
| 8,802,832 | B2 | 8/2014 | Mash et al. |
| 2003/0153552 | A1 | 8/2003 | Mash et al. |
| 2003/0158202 | A1 | 8/2003 | Caldirola et al. |
| 2006/0051317 | A1 | 3/2006 | Batrakova et al. |
| 2007/0185085 | A1 | 8/2007 | Mash |
| 2009/0264653 | A1 | 10/2009 | Bartolini et al. |
| 2010/0249105 | A1 | 9/2010 | Schrimpf et al. |
| 2010/0311722 | A1 | 12/2010 | Mash |
| 2010/0311723 | A1 | 12/2010 | Mash |
| 2010/0311724 | A1 | 12/2010 | Mash |
| 2010/0311725 | A1 | 12/2010 | Mash |
| 2012/0083485 | A1 | 4/2012 | Mash |
| 2012/0253037 | A1 | 10/2012 | Moriarty et al. |
| 2013/0072472 | A1 | 3/2013 | Gless et al. |
| 2013/0131046 | A1 | 5/2013 | Moriarty et al. |
| 2013/0165414 | A1 | 6/2013 | Gless et al. |
| 2013/0165647 | A1 | 6/2013 | Moriarty et al. |
| 2013/0303756 | A1 | 11/2013 | Mash et al. |
| 2014/0179685 | A1 | 6/2014 | Mash et al. |
| 2014/0315837 | A1 | 10/2014 | Mash et al. |
| 2014/0315891 | A1 | 10/2014 | Mash |
| 2014/0357741 | A1 | 12/2014 | Mash et al. |

FOREIGN PATENT DOCUMENTS

| | | | |
|---|---|---|---|
| EP | 2 338 494 | | 6/2011 |
| GB | 0 841 697 | | 7/1960 |
| GB | 0 924 042 | | 4/1962 |
| GB | 1 256 914 | | 12/1971 |
| GB | 1 378 348 | | 12/1974 |
| GB | 2 271 059 | | 4/1994 |
| JP | 01-100188 | | 4/1989 |
| JP | 04-221315 | | 8/1992 |
| JP | 2001-511776 | | 8/2001 |
| JP | 2007-511542 | | 5/2007 |
| WO | WO-91/18609 | A1 | 12/1991 |
| WO | WO-93/20825 | A1 | 10/1993 |
| WO | WO-93/25217 | A1 | 12/1993 |
| WO | WO-94/06426 | A1 | 3/1994 |
| WO | WO-94/14490 | A1 | 7/1994 |
| WO | WO-96/03127 | A1 | 2/1996 |
| WO | WO-98/33802 | | 8/1998 |
| WO | WO-99/11250 | | 3/1999 |
| WO | WO-2005/049627 | | 6/2005 |
| WO | WO-2007/012464 | | 2/2007 |
| WO | WO-2007/070892 | | 6/2007 |
| WO | WO-2010/036998 | | 4/2010 |
| WO | WO-2011/022772 | | 3/2011 |
| WO | WO-2012/012764 | A1 | 1/2012 |
| WO | WO-2012/103028 | | 8/2012 |
| WO | WO-2013/085850 | | 6/2013 |
| WO | WO-2013/085922 | A1 | 6/2013 |
| WO | WO-2013/148572 | | 10/2013 |

OTHER PUBLICATIONS

Office Action on Chinese Application 201280058362.5, issued Aug. 5, 2015, English translation provided.
U.S. Appl. No. 13/566,819, filed Aug. 3, 2012, Mash et al.
U.S. Appl. No. 14/257,841, filed Apr. 21, 2014, Mash, Deborah C.
U.S. Appl. No. 14/298,534, filed Jun. 6, 2014, Mash et al.
U.S. Appl. No. 14/323,743, filed Jul. 3, 2014, Mash et al.
"Analysis—HPLC—Interchim technology", Interchim.com, pp. B31-B93.
Ahuja, Satinder (Ed.), "Chiral Separation Methods for Pharmaceutical and Biotechnological Products", John Wiley & Sons (published on line Oct. 2010).

Ala-Hurula, et al. "Erogotamine Abuse: Results of Ergotamine Discontinuation, with Special Reference to the Plasma Concentrations," Cephalalgia, 2:4 1982, abstract only.
Ala-Hurula, et al. "Tolfenamic Acid and Ergotamine Abuse," Headache, 21:6, 1981, abstract only.
Alexander. "A Procedure for Drug Screening Without the Need to Transport Urines Use of Ion Exchange Papers and Hem Agglutination Inhibition," Clinical Toxicology, 9:3, 1976, abstract only.
Alim, et al. "Open-Label, Dose Run-Up Study of Diethylpropion in Initial Cocaine Abstinence," Clinical Neuropharmacology, 17:2, 1994, abstract only.
Almeida. "Use and Abuse of Alcohol and Drugs a Clinical Study of Certain Aspects of Their Interrelationship," Boletin de la Oficina Sanitaria Panamericana, 88:1, 1980, abstract only.
Al-Shabanah, et al. "Gastric Antiulcer and Cytoprotective Effects of Cathinone, a Psychoactive Alkaloid of Khat (Catha Edulis Forsk.) and Amphetamine in Rats," Regulatory Peptides, abstract only, 1994.
Altman et al., "An Improved Cu-Based Catalyst System for the Reactions of Alcohols with Aryl Halides," J. Org. Chem., (2008), 73(1):284-286.
Azevedo, et al. "Adrenergic Nerve Degeneration Induced by Condensation Products of Adrenaline and Acetaldehyde," Naunyn-Schmiedeberg's Archives of Pharmacology, 300:2, 1977, abstract only.
Bagal, et al. "Modulation of Morphine-Induced Antinociception by Ibogaine and Noribogaine," Brain Research, 741:1-2, 1996, pp. 258-262.
Bartlett, et al. "The Alkaloids of Tabernanthe iboga. Part IV. The Structures of Ibogamine, Ibogaine, Tabernanthine and Voacangine." Journal of the American Chemical Society, 80, 1958, pp. 126-136.
Batrakova. "Pluronic P85 Enhances the Delivery of Digoxin to the Brain: In Vitro and In Vivo Studies", The Journal of Pharmacology and Experimental Therapy, 296, 2001, pp. 551-557.
Baumann et al. "Comparative Neurobiology of Ibogaine and its Metabolite, 12-Hydroxyibogaimine (Noribogaine), in Rodents." Conference at New York University, Abstract only.
Baumann et al., In vivo Neurobiological Effects of Ibogaine and Its o-Desmethyl Metabolite, 12 Hydroxyibogamine (Noribogaine), in Rats, J. Pharmacol. Exp. Ther. 2001, vol. 297, No. 2, pp. 531-539.
Beaubrun. "The Diagnosis and Management of Acute Psychotic Reaction Due to Alcohol and Drugs", Caribbean Medical Journal, 36:1, 1975, abstract only.
Beck, et al. "Energy-Dependent Reduced Drug Binding as a Mechanism of Vinca Alkaloid Resistance in Human Leukemic Lymphoblasts", Molecular Pharmacology, 24:3, 1983, abstract only.
Beesley et al., "Chiral Chromatography", John Wiley & Sons (1998).
Benet, et al. "Pharmacokinetics: Biotransformation of Drugs." In Gilman et al. Goodman and Gilman's the Pharmacological Basis of Therapeutics, 1990, pp. 13-16.
Benoist, et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunology Immunotherapy, 30:5, 1989, abstract only.
Bert, et al. "Non-Amphetaminic Central Stimulation by Alkaloids from the Ibogaine and Vobasine Series", Planta Medicina, 54:3, 1988, abstract only.
Bhargava, et al. "Effects of ibogaine and noribogaine on the antinociceptive action of mu-, delta- and kappa-opioid receptor agonists in mice", Brain Research 752, 1997, pp. 234-238.
Bloomer et al., "Arc/Arg3.1 Translation is controlled by Convergent N-Methyl-D-aspartate and Gs-coupled Receptor Signaling Pathways," J. Bio. Chem. (2008), 283(1):582-592.
Blum, et al. "Peyote a Potential Ethnopharmacologic Agent for Alcoholism and Other Drug Dependencies Possible Biochemical Rationale", Clinical Toxicology, 11:4, 1977, abstract only.
Blum, et al. "Possible Role of Tetrahydroisoquinoline Alkaloids in Postalcohol Intoxication States", Annals of the New York Academy of Science, 273, 1976, abstract only.

(56) References Cited

OTHER PUBLICATIONS

Blum, et al. "Putative Role of Isoquinoline Alkaloids in Alcoholism: A Link to Opiates", Alcoholism: Clinical and Experimental Research, 2:2, 1978, abstract only.
Brady, et al. "Analgesic Effects of Intraventricular Morphine and Enkephalins in Nondependent and Morphine-Dependent Rats," Journal of Pharmacology and Experimental Therapy, 222:1, 1982, abstract only.
Buchi, et al. "The total synthesis of iboga alkaloids," Jounal of the American Chemical Society, 88, 1966, pp. 3099-3109.
Bundgaard. "Design of Prodrugs: Bioreversible Derivatives for Various Functional Groups and Chemical Entities." Design of Prodrugs, 1-10, 1985.
Bussel, et al. "Isolated Thrombocytopenia in Patients Infected with HIV Treatment with Intravenous Gamma Globulin," American Journal of Hematology, 28:2, 1988, abstract only.
Caccamese et al., "Chiral HPLC Separation and CD Spectra of the Enantiomers of the Alkaloid Tacamonine and Related Compounds", Chirality (2001), 13:691-93.
Caldwell, et al. "The Biochemical Pharmacology of Abused Drugs. III. Cannabis, Opiates, and Synthetic Narcotics," Clinical Pharmacological Therapy, 16:6, 1974, abstract only.
Calpus printout of Watts et al. "Alkaloids from Stemmadenia Species", I. Alkaloids of S. Donnellsmithiii and S. Galleottiana, (1958), vol. 2, pp. 173-182.
CALPUS printout of Zetler. "Some Pharmacological Properties of 12 Natural and 11 Partially Synthetic Indole Alkaloids from Tropical Apocyanaceae of the Subtribe Tabernaemontaninae", Arzneimittel-Forschung, (1964), 14:12, pp. 1277-1286.
Cankat. "Pharmacological Aspects of Drug Induced Headache", Functional Neurology, 7:6, 1992, abstract only.
Cappendijk, et al. "The Inhibitory Effect of Norharman on Morphine Withdrawal Syndrome in Rats: Comparison with Ibogaine." Behavioural Brain Research, 65, 1994, pp. 117-119.
Cappendijk, et al. "Inhibitory Effects of Ibogaine on Cocaine Self-Administration in Rats", European Journal of Pharmacology, 241:2-3, 1993, abstract only.
CAS Registry record for "Noribogaine" (1984).
Castle. "Drugs and Fibrotic Reactions—Part I", Adverse Drug React. Bull., 113: abstract only, 1985.
Chaturvedula et al, "New Cytotoxic Indole Alkaloids from Tabe rnaemontana calcarea from the Madagascar Rainforest", Journal of Natural Products, (2003), vol. 66, pp. 528-531.
Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry, 1965.
Chemical abstract, RN 53508-36-4 Registry, 1974.
Chemical abstract, RN 57511-56-5 Registry, 1975.
Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.
Cherny, et al., Opioid responsiveness of cancer pain syndromes caused by neuropathic or nociceptive mechanisms: a combined analysis of controlled, single-dose studies, Neurobiology 44, 1994, pp. 857-861.
Cheze, et al. "Determination of ibogaine and noribogaine in biological fluids and hair by LC-MS/MS after Tabernanthe iboga abuse", Forensic Science International, Elsevierscientific Publishers Ireland Ltd, IE, vol. 176, No. 1, Nov. 19, 2007, pp. 58-66.
CN Office Action for CN Appl. No. 201180038173.7 dated Dec. 10, 2014.
Communication pursuant to Article 94(3) EPC for Appl. No. 11159572.4, dated Apr. 8, 2014.
Communication pursuant to Article 94(3) EPC for Appl. No. 11743404.3, dated Apr. 10, 2014.
Corey, E.J., "Catalytic Enantioselective Diels-Alder Reactions: Methods, Mechanistic Fundamentals, Pathways, and Applications," Angew. Chem. Int. Ed., (2002), 41:1650-1667.
Criel, et al. "Drug Dependent Red Cell Antibodies and Intravascular Haemolysis Occurring in Patients Treated with 9 Hydroxy-Methyl-Ellipticinium," British Journal of Haematology, 46:4, 1980, abstract only.
Damstrup, et al. "Retroperitoneal Fibrosis After Long-Term Daily Use of Ergotamine," International Urology and Nephrology, 18:3, 1986, abstract only.
Database Registry (Online), Chemical Abstracts Service, Columbus Ohis, US Nov. 16, 1984, "ibogamine-18-carboxylic acid, 12-methoxy-,potassium sal," XP002638006, Database accession No. 5500-12-9.
Database Registry Chemical Abstracts Service, Columbus, Ohio, US; 1984, "Ibogamine-18-carboxylic acid, 12-methoxy-, potassium sal", Database accession No. 5500-12-9.
Deecher, et al. "Mechanisms of Action of Ibogaine and Harmaline Congeners Based on Radioligand Binding Studies." Brain Research 571, 1992, pp. 242-247.
Diener, et al. "Analgesic-Induced Chronic Headache Long-Term Results of Withdrawal Therapy," Journal of Neurology, 236:1, 1989, abstract only.
Dierckx, et al. "Intraarterial Sodium Nitroprusside Infusion in the Treatment of Severe Ergotism," Clinical Neuropharmacology, 9:6, 1986, abstract only.
Dzoljic, et al. "Effect of Ibogaine on Naloxone-Precipitated Withdrawal Syndrome in Chronic Morphine-Dependent Rats," Archives Internationales de Pharmacodynamie et de Thérapie, 294, 1988, pp. 64-70.
Eberwine, et al. "Molecular Analysis of Cellular Responses to Opiate Use", Fidia Research Foundation Symposium Series 7 (Neurotransmitter Regulation of Gene Transcription) 1991, abstract only.
Elkind. "Drug Abuse and Headache", Medical Clinics of North America, 75:3, 1991, abstract only.
EP Office Action, Communication Pursuant to Article 94(3) EPC dated Jun. 4, 2013 in related European Patent Application No. 11159572.4.
European extended search report for EP Appl. No. 12763567.0 dated Oct. 20, 2014.
European Office Action dated Apr. 17, 2015 in European Patent Application No. 11743404.
Evenson. "Developments in Therapeutic Drug Monitoring and Alkaloid Analysis", Federation Proceedings, 34:12, 1975, abstract only.
Extended European Search Report dated Jun. 6, 2011 in related European Patent Appl. No. 11159572.4.
Extended European Search Report issued on 12754746,5, mailed Apr. 23, 2015.
Faglia, et al. "Dihydroergocryptine in Management of Microprolactinomas," Journal of Clinical Endocrinology & Metabolism, 65:4, 1987, abstract only.
Fairchild, et al. "Keynote Address: Multidrug Resistance: A Pleiotropic Response to Cytotoxic Drugs," International Journal of Radiation, Oncology, Biology, & Physics, 20:2, 1991, abstract only.
Finkle. "Phencyclidine Identification by Thin-Layer Chromatography. A Rapid Screening Procedure for Emergency Toxicology", American Journal of Clinical Pathology, 70:2, 1978, abstract only.
First Examination Report for Australian Appl. No. 614366, dated Apr. 11, 2014.
First Office Action for Chinese Appl. No. 201180038173.7, dated Mar. 25, 2014.
Fonne-Pfister, et al. "Xenobiotic and Endobiotic Inhibitors of Cytochrome P-450dbl Function, the Target of the Debrisoquine / Sparteine Type Polymorphism," Biochemical Pharmacology, 37:20, 1988, abstract only.
Frances, et al. "Effects of Ibogaine on Naloxone-Precipitated Withdrawal in Morphine-Dependent Mice", Fundamental Clininical Pharmacology, 6:8-9, 1992, abstract only.
Futatsugi, et al., "Oxazaborolidine-Derived Lewis Acid Assited Lewis Acid as a Moisture-Tolerant Catalyst for Enantioselective Diels-Alder Reactions," Angew. Chem. Int. Ed., (2005), 44:1484-1487.

(56) References Cited

OTHER PUBLICATIONS

Gabr, et al. "Changes in Absolute Amount of Alkaloids in Datura-Metel Treated with Certain Growth Regulators", Herba Pol, 21:2, 1975, abstract only.
Garcia, et al. Chronic pain states: pathophysiology and medical therapy, Seminars in Arthritis and Rheumatism, 27, 1997, pp. 1-16.
Gennaro. "Remington: The Science and Practice of Pharmacy", Mack Publishing Col., vol. II, 1995, pp. 1736 & 1814.
George, et al. "Palliative medicine", Postgraduate Medical Journal, vol. 69, 1993, pp. 426-449.
Gifford, A. N. and Johnson, K. Gifford, et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41:4, 1992, abstract only.
Glick, et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657, 1994, pp. 14-22.
Glick, et al. "Effect of Ibogaine on Acute Signs of Morphine Withdrawal in Rats: Independence from Tremor", Neuropharmacology, 31:5, 1992, abstract only.
Glick, et al. "Effects of Aftereffects of Ibogaine on Morphine Self-Administration in Rats", European Journal of Pharmacology, 195:3, 1991, abstract only.
Glick, et al. "Ibogaine-like effects of noribogaine in rats", Brain Research, 713, 1996, pp. 294-297.
Glick, et al. "Local Effects of Ibogaine on Extracellular Levels of Dopamine and Its Metabolites in Nucleus Accumbens and Striatum: Interactions with D-Amphetamine", Brain Research, 628:1-2, 1993, abstract only.
Gold, et al. "Effect of Methadone Dosage on Clonidine Detoxification Efficacy", American Journal Psychiatry, 137:3, 1980, abstract only.
Gothoni. "Harmine-, Lon-954- and 5-Hydroxytryptophan-Induced Tremors in Rats Withdrawn from Ethanol", Acta Pharmacologica et Toxicologica, Copenhagen, DK, 57:1, 1985, abstract only.
Greenwald, et al., "Poly(ethylene glycol) conjugated drugs and prodrugs: a comprehensive review," Crit. Rev. Ther. Drug Carrier Syst., (2000), 17(2):101-161.
Gross. "Effect of Ergot Alkaloids on Serum Prolactin in Non-Psychotic Organic Brain Syndrome of the Eldely", Experimental Aging Research, 5:4, 1979, abstract only.
Gunn. "Relations Between Chemical Constitution, Pharmacological Actions, and Therapeutic Uses, in the Harmine Group of Alkaloids." From the Pharmacological Laboratory, University of Oxford, 1935, pp. 379-396.
Haber, et al. "Tetrahydroisoquinolines—Endogenous Products After Chronic Alcohol Abuse", Pharmazie, 47:1, 1992, abstract only.
Halikas, et al. "Treatment of Crack Cocaine Use with Carbamazepine", American Journal of Drug and Alcohol Abuse, 18:1, 1992, abstract only.
Hanks. "Opioid-responsive and opioid-non-responsive pain in cancer," British Medical Bulletin 47, 1991, pp. 718-731.
Hardman, et al. "Goodman & Gilman's The Pharmacological Basis of Therapeutics" (9th ed, 1996) p. 51 and pp. 57-58.
Harsing, et al. "Evidence that Ibogaine Releases Dopamine from the Cytoplasmic Pool in Isloated Mouse Striatum", Journal of Neural Transmission General Section, 96:3, 1994, abstract only.
Hearn, et al. "Identification and Quantitation of Ibogaine and an o-Demethylated Metabolite in Brain and Biological Fluids Using Gas Chromatography—Mass Spectrometry." Journal Analytical Toxicology, 19, 1995, pp. 427-434.
Heel, et al. "Buprenorphine: A Review of Its Pharmacological Properties and Therapeutic Efficacy", Drugs, 17:2, 1979, abstract only.
Henry, et al. "Reversible Cerebral Arteriopathy Associated with the Administration of Ergot Derivatives", Cephalalgia, 4:3, 1984, abstract only.

Ho, et al. "Metabolism of Harmaline in Rats." Biochemical Pharmacology vol. 20, 1971, pp. 1313-1319.
Hoes. "Clinical Criteria for the Selection of Anxiolytics", Tijdschrift voor Therapie Geneesmiddel en Onderzoek, 9:9, 1984, abstract only.
Holbrook. "Nicotine Addiction." In Isselbacher et al. (ed.), "Harrison's Principals of Internal Medicine" 13th Ed., McGraw-Hill Inc., 1994, 2433-2437.
Holzner, et al. "The Neuroleptic Sleeping Course in Chronic Headache", Therapiewoche, 35/36: 1985, abstract only.
Huang, et al. "Cytotoxicity and Sister Chromatid Exchanges Induced in Vitro by Six Anticancer Drugs Developed in the People's Republic of China", Journal of the National Cancer Institute, 71:4, 1983, abstract only.
Hubens, et al. "Chronic Intake of a Hydrogenated Ergot Alkaloid Causing Peripheral Vascular Ischemia—A Case Report", Journal of Vascular Surgery, 21:4, 1987, abstract only.
Huffman, et al. "A Formal Synthesis of (±)-Ibogamine," Journal of Organic Chemistry, vol. 50, 1985, pp. 1460-1464.
International Preliminary Report on Patentability for PCT/US2012/067799, dated Jun. 19, 2014.
International Preliminary Report on Patentability for PCT/US2012/071052, issued Jun. 23, 2015.
International Search Report and Written Opinion dated Mar. 11, 2013 in related PCT Patent Application No. PCT/US12/71052.
International Search Report and Written Opinion dated Oct. 31, 2012 in related PCT Application No. PCT/US2012/030405.
International Search Report and Written Opinion dated Oct. 4, 2012 in related PCT Application Serial No. PCT/US2012/022255.
International Search Report for PCT/US2011/045081 dated Oct. 4, 2011.
Isler. "Treatment of Headache", Schweizerische Medizinische Wochenschrift, 114:35, 1984, abstract only.
Jaffe. "Drug Addiction and Drug Abuse", Goodman and Gilman's The Pharmacological Basis of Therapeutics, 8th Ed., date unknown, pp. 520-523 & pp. 559-568.
Jaffe. "Psychopharmacology and Opiate Dependence," U.S. Public Health Services Publication, 1957-1967: pp. 1836.
James. "Linkers for solid phase organic synthesis," Tetrahedron, 55, 1999, pp. 4855-4946.
Jana et al., "Progress in the Synthesis of Iboga-alkaloids and their Congeners," Organic Preparation and Procedures International, (2011), 43:541-573.
Jana et al., "Total synthesis of ibogaine, epiibogaine and their analogues", Tetrahedron. 2012. vol. 68, pp. 7155-7165.
Jane, et al. "High-Performance Liquid Chromatographic Analysis of Basic Drugs on Silica Columns Using Non-Aqueous Ionic Eluents. II. Application of UV, Fluorescence and Electrochemical Oxidation detection", Journal of Chromatography, 323:2, 1985, abstract only.
Jansen, et al. "Ethnopharmacology of Kratom and the Mitragyna Alkaloids", Journal of Ethnopharmacology, 23:1, 1988, abstract only.
Janzen. "History of Use of Psychotropic Drugs in Central Africa," Psychotropes, 1/2: 1983, abstract only.
Jarraya, et al., "N-(Hydroxymethyl)ibogaine," Acta Cryst., (2008), E64—vol. 64(9):o1739.
Justins. "Management strategies for chronic pain," Annals of the Rheumatic Diseases, vol. 55, 1996, pp. 588-596.
Kagan, et al., "Catalytic Asymmetric Diels-Alder Reactions," Chem. Rev., (1992), 92:1007-1019.
Kalix. "Khat: A Plant with Amphetamine Effects," Journal of Substance Abuse Treatment, 5:3, 1988, abstract only.
Kalix. "Pharmacological Properties of the Stimulant Khat", Pharmacological Therapy, 48:3, 1990, abstract only.
Keefner. "A Gas Chromatography—Mass Spectrometry (GCMS) Method for Ibogaine", Society for Neuroscience Abstracts, 19:1-3, 1993, abstract only.
Keller, et al. "Modulation of Neopterin Release by Human Kupffer Cells in Culture: Possible Implication in Clinical Monitoring of HIV-Seropositive Subjects", Cells Hepatic Sinusoid, 3: 1991, abstract only.
Kingston et al., "Cytotoxicity of Modified Indole Alkaloids", Journal of Pharmaceutical Sciences, 68:11, Nov. 1979, pp. 1403-1405.

(56) References Cited

OTHER PUBLICATIONS

Knoll. "Azidomorphines and Homopyrimidazols: A New Approach to the Ideal Analgetic," ACTA Physiologica et Pharmacologica Bulgarica, 3:2, 1977, abstract only.
Knoll. "Azidomorphines: A New Family of Potent Analgesics with Low Dependence Capacity," Progress in Neuro-Psychopharmacology and Biological Psychiatry, 3:1-3, 1979, abstract only.
Koch, et al. "Drug-Induced Liver Injury in Liver Biopsies of the Years 1981 and 1983, their Prevalence and Type of Presentation", Pathology, Research and Practice, 179: 1985, abstract only.
Konig. "Psychiatric Intensive Therapy After Acute Alkaloid Withdrawal Syndrome", Infusionsther Klin Ernahr, 6:1, 1979, abstract only.
Kontrimaviciute et al., "Liquid chromatography-electrospray mass spectrometry determination of ibogaine and noribogaine in human plasma and whole blood: Application to a poisoning involving Tabernanthe iboga root" J. Chromatog. B (2006), 843, 131-41.
Kornetsky. "Pharmacology Drugs Affecting Behavior." John Wiley & Sons, 1976, pp. 185-187.
Kostowski, et al. "The Effects of Some Hallucinogens on Aggressiveness of Mice and Rats" Pharmacology, 7, 1972, pp. 259-263.
Krug. "Cocaine Abuse: Historical, Epidemiologic, and Clinical Perspectives for Pediatricians", Advances in Pediatrics, 36:369-406, 1989.
Kuehne et al., "Biomimetric syntheses of indole alkaloids. 11. Syntheses of .beta.-carboline and indoloazepine intermediates," J. Org. Chem., (1985), 50(7):919-924.
Kupers, et al. "Morphine differentially affects the sensory and affective pain ratings in neuorgenic and idiopathic forms of pain." Pain, 47, 1991, pp. 5-12.
Kuroch et al., "Voacanga Africana: Chemistry, Quality and Pharmacological Activity" ACS Symposium Series 1021 (African Natural Plant Products), (2009), 363-80.
Lakoski, et al. "Electrophysiologic Characterization of an Ibogaine Metabolite in Dorsal Raphe Nucleus and Hippocampus." Society for Neuroscience, 21:716, 1995, abstract only.
Larson-Prior, et al. "Electrophysiologic Characterization of an Ibogaine Metabolite in the Cerebellar Cortex." Society for Neuroscience, 21:716, 1995, abstract only.
Layer, et al., "Structurally modified ibogaine analogs exhibit differing affinities for NMDA receptors," European Journal of Pharmacology, 1996, 309:159-165.
Lemontt, et al. "Increase MDR Gene Expression and Decreased Drug Accumulation in Multidrug-Resistant Human Melanoma Cells", Cancer Research, 48:22, 1988, abstract only.
Leonard, J. "A Practical Introduction to Separation and Purification techniques for the Beginning Organic Chemistry Laboratory", Chem. Ed. (1981), 58, 1022-23.
Leoni, et al. "Effect of Cocaine and Morphine on Neutral Endopeptidase Activity of Human Peripheral Blood Mononuclear Cells Cultures with Lectins," Cell Biochemistry and Function, 11:3, 1993, abstract only.
Lerida, et al. "Incidence of Morphine Withdrawal and Quasi-Abstinence Syndrome in a Model of Chronic Pain in the Rat," Neuroscience, 81:1-2, 1987, abstract only.
Lewis, "Studies on the synthesis and biosynthesis of indole alkaloids", The Faculty of Graduate Studies Department of Chemistry University of British Columbia, (1978), See compound 220, Figure 57. abstract only.
Lewis, et al. "Adverse Reactions and Interactions with .beta.-Adrenoceptor Blocking Drugs," Journal of Medical Toxicology, 1:5, 1986, abstract only.
Lewis, et al. "Narcotic Analgesics and Antagonists," Annual Review of Pharmacology, 11, 1971, abstract only.
Licht, et al. "Induction of Multiple-Drug Resistance During Anti-Neoplastic Chemotherapy In-Vitro," International Journal of Cancer, 49:4, 1991, abstract only.
Ling, et al. "Drugs of Abuse-Opiates", in Addtiction Medicine [Special Issue], Western Journal of Medicine, 152, 1990, pp. 565-572.
Low, et al. "Effects of Acronycine and Cytouchalasin B on the Division of Rat Leukemia Cells," Experimental Cell Research, 131:1, 1981, abstract only.
Ma, et al. "Inhibition of Respiratory Burst Activity in Alveolar Macrophages by Bisbenzylisoquinoline Alkaloids: Characterization of Drug-Cell Interaction", Experimental Lung Research, 18:6, 1992, abstract only.
Maisonneuve, et al. "Interactions of Ibogaine and D-Amphetamine: in vivio Microdialysis and Motor Behavior in Rats." Brain Research 579, 1992, pp. 87-92.
Maisonneuve, et al. "Acute and Prolonged Effects of Ibogaine on Brain Dopamine Metabolism and Morphine-Induced Locomotor Activity in Rats", Brain Research, 575:1, 1992, abstract only.
Maisonneuve, et al. "Interactions Between Ibogaine, a Potential Anti-Addictive Agent, and Morphine: an in Vivo Microdialysis Study," European Journal of Pharmacology, 199:1, 1991, abstract only.
Martellotta, et al. "Effects of the Calcium Antagonist Isradipine on Cocaine Intravenous Self-Administration in Rats", Psychopharmacologia, 113:3-4, 1994, abstract only.
Martin, et al. "Neuropathic Pain in Cancer Patients: Mechanisms, Syndromes, and Clinical Controversies," Journal of Pain and Symptom Management, 14:2, 1997, pp. 99-117.
Mash, et al. "Ibogaine in the Treatment of Heroin Withdrawal," The Alkaloids 56, 2001, pp. 1-17.
Mash, et al. "Ligand Binding Profiles of Ibogaine and its O-demethylated Metabolite Noribogaine: Implications for Developing Novel Multi-target Anti-addiction Agents." Society of Neurosciences, vol. 21, 1995, abstract only.
Mash, et al. "Preclinical screening of an ibogaie metabolite (noribogaine) on cocaine-induced hyperlocomotion and cocaine self-administration." Society of Neurosciences, vol. 22, 1996, abstract only.
Mash, et al. "Properties of Ibogaine and its Principle Metabolite (12-hydroxyibogamine) at the MK-801 binding site of the NMDA receptor complex," Neuroscience Letters, 192, 1995, pp. 53-56.
Mateer, et al. "Reversible Ipecac Myopathy," Archives of Neurology, 42:2, 1985, abstract only.
Matharu, et al. "Preformulation and Development of Ibogaine Injection for the Treatment of Drug Abuse," Pharmaceutical Research, 10: 1993, abstract only.
Mattingly, et al. "Selective Antagonism of Dopamine D Sub 1 and D Sub 2 Receptors Does Not Block the Development of Behavioral Sensitization to Cocaine," Psychopharmacologia, 114:2, 1994, abstract only.
McNeish, et al. "The 5-HT Sub 3 Antagonist Zacopride Attenuates Cocaine-Induced Increases in Extracellular Dopamine in Rat Nucleus Accumbens," Pharmacology, Biochemistry, and Behavior, 45:4, 1993, abstract only.
Melchior, et al. "Preference for Alcohol Evoked by Tetra Hydro Papaveroline Chronically Infused in the Cerebral Ventricle of the Rat," Pharmacol Biochem Behav, 7:1, 1977, abstract only.
Mendelson & Mello "Cocaine and Other Commonly Abused Drugs." In Isselbacher et al. (ed.), "Harrison's Principals of Internal Medicine." 13th Ed., McGraw-Hill Inc., 1994, pp. 2429-2433.
Menzies, et al. "Gangrene of the Small Bowel: A Complication of Methysergide Therapy," Australian and New Zealand Journal of Surgery, 52:5, 1982, abstract only.
Metelitsa. "Pharmacological Agents in Controlling Smoking," Biull Vsesoiuznogo Kardiol Nauchn Tsentra, 10:1, 1987, abstract only.
Millan. "k-Opioid Receptors and Analgesia," Trendes in Pharmacologicla Sciences, 11, 1990, pp. 70-76.
Mizuhashi, et al. "Antitumor Activities of IKP-104 A 4-1H Pyridizinone Derivative on Cultured and Implanted Tumors," Japanese Journal of Cancer Research, 81:12, 1990, abstract only.
Montefiori, et al. "In Vitro Evaluation of Mismatched Double-Stranded RNA (Ampligen) for Combination Therapy in the Treatment of Acquired Immunodeficiency Syndrome," AIDS Research and Human Retroviruses, 5:2, 1989, abstract only.
Mulamba, et al. "Alkaloids from Tabernathe Pubescens," Journal of Natural Products, vol. 44:2, 1981, pp. 184-189.

(56) References Cited

OTHER PUBLICATIONS

Naikwadi et al., "Liquid Chromatography of Phenolic Compounds on a Microbore Anion Exchange Resin Column," Analytical Chemistry, 56:8, 1984, p. 1525-1527.
Naranjo. "Ibogaine in psychotherapy: psychoanalysis according to Naranjo", part IV, pp. 1-2. http://www.nettuno.it/fiera/electric.italy/bwitif:html (1969).
Niemann et al, "The Isolation of Rupicoline and Montanine, Two Pseudoindoxyl Alkaloids of Tabernaemontana Rupicola Benth", The Journal of Organic Chemistry, 31(7):2265-2269.
Nishiyama, et al. "Expression of the Multidrug Transporter, P-Glycoproteiin, in Renal and Transitional Cell Carcinomas," Cancer, 71:11, 1993, pp. 3611-3619.
Nooter, et al. "Multidrug Resistance (MDR) Genes in Haematological Malignancies," Cytotechnology, 12:1-3, 1993, abstract only.
Nunn-Thompson, et al. "Pharmacotherapy for Making Cessation", Clin Pharm, 8:10, 1989, abstract only.
Obach, et al., "Cythochrome P4502D6 Catalyzes the O-Demethylation of the Psychoactive Alkaloid Ibogaine to 12-Hydroxyibogamine," Drug Metabolism and Disposition 26:8, 1998, pp. 764-768.
Office Action for Israeli Patent Application No. 227593 dated Nov. 13, 2013.
Office Action on Japanese Application 2013-520892, mailed Jul. 7, 2015.
O'Hearn, et al. "Degenration of Prukinje Cells in Parasagittal Zones of the Cerebellar Vermis After Treatment with Ibogaine of Harmaline," Neuroscience, 55:2, 1993, abstract only.
O'Hearn, et al. "Ibogaine Induces Glial Activation in Parasagittal Zones of the Cerebellum," Neuroreport, 4:3, 1993, abstract only.
Pablo, et al, "Noribogaine Stimulates Naloxone-Sensitive[35S]GTPgammaS Binding," NeuroReport, 9, 1998, pp. 109-114. (Website Publication Date of Dec. 20, 1997.).
Pacifici, et al. "Immunological Effect of Cocaine and Host Resistance in Mice," International Journal of Immunotherapy, 8:2, 1992, abstract only.
Palyi. "Survivial Responses to New Cytostatic Hexitols of P388 Mouse and K562 Leukemia Cells in Vitro," Cancer Treatment Reports, 70:2, 1986, abstract only.
Pantazis, et al. "Efficacy of Camptothecin Congeners in the Treatment of Human Breast Carcinoma Xenografts," Oncology Research, 5:8, 1994, abstract only.
PCT International Preliminary Report on Patentability dated Jul. 30, 2013 in related PCT International Patent Application No. PCT/US2012/022255.
PCT International Preliminary Report on Patentability for PCT/US2012/067629 dated Nov. 13, 2014.
PCT International Search Report and Written Opinion dated Dec. 8, 2014 for PCT Application No. PCT/US2014/031364.
PCT International Search Report and Written Opinion dated Jan. 21, 2015 in PCT Patent Application No. PCT/US2014/034826.
PCT International Search Report and Written Opinion for related PCT/US2013/022874, dated Jun. 28, 2013.
PCT International Search Report and Written Opinion in related PCT Patent Application No. PCT/US12/67799, dated Mar. 28, 2013.
PCT International Search Report in PCT/US2012/067629 dated Mar. 13, 2013.
Pehek. "Effects of Cathinone and Amphetamine on the Neurochemistry of Dopamine in Vivo," Neuropharmacology, 29:12, 1990, abstract only.
Percheron et al., Ibogaine et vocangine. Compt. Rend. Acad. Sci., (1957), 245:1141-1143.
Perera, et al. "Tertiary Indole Alkaloids of Tabernaemontana Dichotoma Seeds," Planta Medica, 49:1, 1983, abstract only.
Perrin. "Clinical Pharmacokinetics of Ergotamine in Migraine and Cluster Headache," Clinical Pharmacokinetics, 10:4, 1985, abstract only.
Popik, et al. "NMDA Antagonist Properties of the pUtative Antiaddictive Drug, Ibogaine," Journal of Pharmaceutical and Experimental Therapeutics, 275:2, 1995, pp. 753-760.
Popik, et al. "The Putative Anti-Addictive Drug Ibogaine is a Competitive Inhibitor of (SUP 3 H) Binding to the NMDA Receptor Complex", Psychopharmacologia, 114:4, 1994, abstract only.
Popik, et al. "100 Years of Ibogaine: Neurochemical and Pharmacological Actions of a Putative anti-addictive Drug," Pharmacological Reviews 47:2, 1995, pp. 235-253.
Pulvirenti, et al. "Lisuride Reduces Intravenous Cocaine Self-Administration in Rats," Pharmacology, Biochemistry and Behavior, 47:4, 1994, abstract only.
Qiu, et al. "The Influence of Chronic Nicotine Treatment on Stress-Induces Gastric Ulceration and Emptying Rate in Rats," Experientia, 48:4, 1992, abstract only.
Radouco-Thomas, et al. "Adverse effects to Psychotomimetics. Proposition of a Psychopharmacological Classification." Pharmacologie, Toxicologie, et abus des psychotomimetiques (hallucinogens), (1974), 109, abstract only.
Rezvani, et al. "Noribogaine, a Primary Ibogaine Metabolite, Reduces Alcohol Intake in P and Fawn-Hooded Rats." RSA Annual Scientific Meeting, 1995, abstract only.
Rezvani, et al. "Reduction of Alcohol Intake in Alcohol Preferring Fawn-hooded and P Rats by Noribogaine, the Primary Metabolite of Ibogaine." NIDA Monograph Series 162:281, 1996, Abstract only.
Ricceri, et al. "Postnatal cocaine Esposure Affects Neonatal Passive Avoidance Performance and Cholinergic Development in Rats," Pharmacology, Biochemistry and Behavior, 45:2, 1993, abstract only.
Rodriguez, et al. "Cocaine Adminstration Prior to Reactivation Facilitates Later Acquisition of an Avoidance Response in Rats," Psychopharmacologia, 112:2-3, 1993, abstract only.
Rosenmund, et al. "Ibogamin, Ibogain and Epiibogamin" Chemische Berichte, 108, 1975, pp. 1871-1895.
Sachs, et al. "Corneal Complications Associated with the Use of Crack Cocaine," Ophthalmology, 100:2, 1993, abstract only.
Salmoiraghi, et al. "Effects of LSD 25, BOL 148, Bufotenine, Mescaline and Ibogaine on the Potentiation of Hexobarbital Hypnosis Produced by Serotonin and Reserpine." Journal of Pharmacology and Experimental Therapeutics 120:1, 1957, pp. 20-25.
Samadi-Baboli, et al. "Preparation of Low Density Lipoprotein-9-Methoxy-Illipticin Complex and Its Cytotoxic Effect Against L1210 and P 388 Leukemic Cells in Vitro," European Journal of Cancer and Clinical Oncology , 25:2, 1989, abstract only.
Saper, et al. "Ergotamine Tartrate Dependency: Features and Possible Mechanisms," Clinical Neuropharmacology, 9:3, 1986, abstract only.
Schecter, et al. "Comparison of the Behavioral Effects of Ibogaine from Three Sources: Mediation of Discriminative Activity," European Journal of Pharmacology, 249:1, 1993, abstract only.
Schneider, et al. "Analysis of the Cardiovascular Action of Ibogaine Hydrochloride." Archives Internationales de Pharmacodynamie et de Thérapie, 110, 1957, pp. 92-102.
Schneider, et al. "Neuropharmacological Studies of Ibogaine: An Indole Alkaloid with Central Stimulant Properties." Annals of the New York Academy of Sciences, 66, 1957, pp. 765-776.
Schneider, et al., "Potentiation Action of Ibogaine on Morphine Analgesia" Experiential, 12, 1956, pp. 323-324.
Schnider, et al. "Use and Abuse of Analgesics in Tension-Type Headache," Cephalalgia, 14:2, 1994, abstract only.
Schuckit & Segal. "Opiod Drug Use." In Isselbacher et al. (ed.), "Harrison's Principals of Internal Medicine" 13th Ed., McGraw-Hill Inc., 1994, 2425-2429.
Schuckit. "Alcohol and Alcoholism," In Isselbacher et al. (ed.), "Harrison's Principals of Internal Medicine." 13th Ed., McGraw-Hill Inc., 1994, pp. 2420-2425.
Seeber, et al. "In Vivo Resistance Towards Anthracyclines, Etoposide, and Cis-Diamminedichloroplatinum (II)," Cancer Research, 42:11, 1982, abstract only.
Sehested, et al. "The Carboxylic Ionophore Monensin Inhibits Active Drug Efflux and Modulates In-Vitro Resistance in Daunorubicin Resistant Enrlich Ascites Tumor Cells," Biochemical Pharmacology, 37:17, 1988, abstract only.
Sershen, et al. "Ibogaine Antagonizes Cocaine-Induced Locomotor Stimulation in Mice," Life Sciences, 50:15, 1992, abstract only.

(56) References Cited

OTHER PUBLICATIONS

Sershen, et al. "Ibogaine Reduces Amphetamine-Induced Locomotor Stimulation in C57BL/6By Mice, but Stimulates Locomotor Activity in Rats," Life Sciences, 51:13, 1992, abstract only.
Sershen, et al. "Ibogaine Reduces Preference for Cocaine Consumption in C57BL/6By Mice," Pharmacology Biochemistry and Behavior, 47:1, 1994, abstract only.
Shen, et al. "Antagonists at Excitatory Opioid Receptors on Sensory Neurons in Culture Increase Potency and Specificity of Opiate Analgesics and Attenuate Development of Tolerance/ Dependence," Brain Research, 636:2, 1994, abstract only.
Sheppard. "A Preliminary Investigation of Ibogaine: Case Reports and Recommendations for Further Study." Journal of Substance Abuse Treatment, 11:4, 1994, abstract only.
Shir, et al. "Neuropathic pain unrelieved by morphine, alleviated by haloperidol," Harefuah 118:8, 1990, abstract only.
Shook et al. "A cyclic Somatostatin Analog that Precipitates Withdrawal in Morphine-Dependent Mice", NIDA Res. Monogr., 76(Probl. Drug Depend.): abstract only, 1987.
Sinkula, et al. "Rationale for Design for Biologically Reversible Drug Derivatives: Prodrugs." Journal of Pharmaceutical Sciences, 64:2, 1975, pp. 181-210.
Sjostromt et al., "Ion Exchange Separation Method for Microdetermination of Tropane Alkaloids in the Presence of Mkphine," 1959, XP55182014.
Slotkin, et al. "A Model of Harmine Metabolism in the Rat." The Journal of Pharmacology and Experimental Therapeutics, 174:3, 1970, pp. 456-462.
Slotkin, et al. "Blood Levels and Urinary Excretion of Harmine and its Metabolites in Man and Rats." The Journal of Pharmacology and Experimental Therapeutics, 173:1, 1970, pp. 26-30.
Slotkin, et al. "Urinary Metabolites of Harmine in the Rat and their Inhibition of Monoamine Oxidase." Biochemical Pharmacology, 19, 1970, pp. 125-131.
Sloviter, et al. "A Common Mechanism of Lysergic Acid, Indolealkylamine and Phenethylamine Hallucinogens: Serotonergic Mediation of Behavioral Effects in Rats." Journal of Pharmacological Experimental Therapy, 214:2, 1980, pp. 231-238.
Smith. "Interaction of Biogenic Amines with Ethanol," Advances in Experimental Medicine and Biology, 56, 1975, abstract only.
Snyder, et al., "Practical HPLC Method Development", 1997, 2nd Ed., pp. 214-218, 266, 267, 282 & 283, John Wiley & Sons, Inc.
Solinas, et al. "Solid-Supported Reagents and Catch-and-Release Techniques in Organic Synthesis", Synthesis 2007:16, 2007, pp. 2409-2453.
Stahl, et al., "Handbook of Pharmaceutical Salts", 1998, p. 250 John Wiley & Sons.
Stella. "Pro-drugs as Novel Drug Delivery Systems", ed. Higuchi, T. et al., American Chemical Society, Washington D.C., 1975, pp. 1-49.
Stella. "Pro-drugs: An Overview and Definition." Prodrugs as Novel Drug Delivery System. ACS Symposium Series: 1975, pp. 1-115.
Stevenson et al, (Ed.), "Chiral Separations", Plenum Press (1987).
Still, et al., "Rapid Chromatorgraphic Technique for Preparative Separations with Moderate Resolutions", J. Org. Chem., (1978), 43, 2923-25.
Sugiyama, et al. "Quantitative Analysis of Cell-Kill Effects of Anticancer Drugs: Consideration of Both In Vitro and In Vivo Expreimental Systems." Gan to Kagaku Ryoho, 14:12, 1987, abstract only.
Suvarna et al., "Hydrolysis of N-Methyl-D-aspartate Receptor-Stimulated cAMP and cGMP by PDE4 and PDE2 Phosphodiesterases in Primary Neuronal Cultures of Rat Cerebral Cortex and Hippocampus," J. Pharmacol. Exp. Ther., (2002), 302(1):249-256.
Tarnower, et al., "Ergotism Masquerading as Arteritis," Postgraduate Medicine, 85:1, 1989, abstract only.
Teoh, et al. "Buprenorphine Effects on Morphine- and Cocaine-Induced Subjective Responses by Drug-Dependent Men," Journal of Clinical Psychopharmacology, 14:1, 1994, abstract only.

Tfelt-Hansen, et al. "Nitroglycerin for Ergotism. Experimental Studies in Vitro and in Migraine Patients and Treatment of an Overt Case," European Journal of Clinical Pharmacology, 22:2, 1982, abstract only.
Third Office Action on Chinese Application 201180038173.7, issued Jun. 17, 2015—English translation provided.
Toda, Fumio (Ed.), "Enantiomer Separation: Fundamentals and Practical Methods", Kluwer Academic Publishers (2004).
Torrenegra, et al. "Alkaloids of stemmadenia grandiflora", Phytochemistry, 27:6, 1988, pp. 1843-1848.
Toyo'oka, "Resolution of chiral drugs by liquid chromatography based upon diastereomer formation with chiral derivatization reagents", J. Biochem. Biophys. Methods 54, 25-56 (2002).
Trost, et al., "A Total Synthesis of Racemic and Optically Active Ibogamine. Utilization and Mechanism of a New Silver Ion Assisted Palladium Catalyzed Cyclization," J. Am. Chem. Soc., (1978), 100(12):3930-3931.
Trost, et al., "Stereocontrolled Approach to 1,4-Disubstitued 1,3-Dienes," J. Org. Chem., (1978), 43(24):4559-4564.
Tsuruo. "Multidrug Resistance: A Transport System of Antitumor Agents and Xenobiotics," Princess Takamatsu Symp, 21, 1990, abstract only.
Uldry, et al. "Cerebrovascular Accidents in Relation to Drug Consumption or Drug Abuse," Schweizerische Rundschau Fur Medizin Praxis, 78:23, 1989, abstract only.
US Office Action on 364105-0502 DTD Dec. 29, 2011.
Valadez, et al. "Persistence of the Ability of Amphetamine Preexposure to Facilitate Acquistion of Cocaine Self-Administration," Pharmacology, Biochemistry and Behavior, 47:1, 1994, abstract only.
Valencia, et al. "Obovatine, a New Bisindole Alkaloid from Stemmadenia Obovata," Journal of Natural Products, 58:1, 1995, pp. 134-137.
Vescovi, et al. "Successful Treatment of Opiate Withdrawal Using Lysine Acetylsalicylate," Current Therapeutic Research, Clinical and Experimental, 33:5, 1983, abstract only.
Villalba, et al. "Uses and Abuses of Ipecacuana Syrup", Farmacia Clinica, 9:1, 1992, abstract only.
Wells, et al. "Recognition and Treatment of Arterial Insufficiency from Cafergot," Journal of Vascular Surgury, 4:1, 1986, abstract only.
Whitaker, et al. "High Affinity 3H-Serotonin Binding to Caudate: Inhibition by Hallucinogenic and Serotonergic Drugs," Psychopharmacology 59, 1978, pp. 1-5.
Whitaker, et al. "Selective Labeling of Serotonin Receptors by d'(3H)Lysergic Acid Diethylamide in Calf Caudate." Proceedings of the National Academy of Sciences 75:12, 1978, pp. 5783-5787.
Whittaker, et al. "Recurrent Laryngeal Nerve Paralysis in Patients Receiving Vincristine and Vinblastine", British Medical Journal, 1:6071, 1977, abstract only.
Widler, et al. "Pharmacodynamics and Pharmacokinetics of Khat: a Controlled Study," Clinical Pharmacology Therapy, 55:5, 1994, abstract only.
Wildmann. "Heterocycles as Physiological Ligands for the Benzodiazepine Receptor and for Other Binding Sites", Pharmacology Residency, 21:6, 1989, abstract only.
Williams, et al. "The 'Alice in Wonderland' Experience Ergot Alkaloid Therapy for Prolactin-Secreting Pituitary Tumors," The Western Journal of Medicine, 138:3, 1983, abstract only.
Wishart, et al. "Is Multidrug Resistance Relevant in Breast Cancer," European Journal of Surgical Oncology, 17:5, 1991, abstract only.
Witt, et al. "Pharmacodynamic and Pharmacokinetic Characterization of Poly(Ethylene glycol) Conjugation to Met-Enkephalin Analog [D-Pen2,D-Pen5]-enkephalin (DPDPE)", Journal of Pharmcological and Experimental Therapy, 298:2, 2001, pp. 848-856.
Witt, et al. "Pluronic P85 Block Copolymer Enhances Opioid Pepetide Analgesia," Journal of Pharmcology and Experimental Therapy, 303:2, 2002, pp. 760-767.
Worz. "Effects and Risks of Psychotropic and Analgesic Combinations," American Journal of Medicine, 75:5A, 1983, abstract only.

(56) References Cited

OTHER PUBLICATIONS

Yang, et al., "Prodrug based optimal drug delivery via membrane transporter/receptor," Expert. Opin. Biol. Ther., (2001), 1(2):159-175.
Zetler, et al. "Pharmacokinetics in the Rat of the Hallucinogenic Alkaloids Harmine and Harmaline." Naunyn-Schmiedeberg's Archives of Pharmacology, 285, 1974, pp. 273-292.
Zetler, et al. "Cerebral Pharmacokinetics of Tremor-Producing Harmala and Iboga Alkaloids" Pharmacology, 7:4, 1972, pp. 237-248.
Communication issued on EP 11743404.3, mailed Nov. 16, 2015.
Glick SD et al., Development of novel medications for drugs addiction. The legacy od an African shrub. AnnN.Y.Acad.Sci. 2000; 909:808-103 abstract[on-line] [found on Aug. 21, 2015]www.ncbi.nlm.nih.gov/pubmed/10911925.
International Search Report & Written Opinion for PCT/US2014/013063 dated Oct. 8, 2015.
Office Action on Russian Application 2013102923/15 dated Aug. 11, 2015 English translation provided.
Peterson, A. L. et al., Treatment of Parkinson's disease with trophic factors. Neurotherapeutics, 2008, vol. 5, No. 2, pp. 270-280.
RN:5500-12-9,REGISTRY (STN) [online], Nov. 16, 1984.
RN:766444-34-2,REGISTRY (STN) [online], Oct. 20, 2004.
Wang et al., Targeted Delivery of GDNF through the Blood-Brain Barrier by MRI-Guided Focused Ultrasound, PLoS One, vol. 7, Issue 12, Article e52925, internal pp. 1-8, Dec. 2012.
Examination Report issued on Australian Application 2012209332, mailed Feb. 10, 2016.
Second Office Action issued on Chinese Application 201280058362.5, mailed Feb. 22, 2016 English translation included.
Office Action issued on Chinese Application 201180038173.7, mailed Jan. 8, 2016, English translation provided.
Office Action issued on Russian Application 2013139382, mailed Dec. 4, 2015, English translation provided.
Russian Office Action on Application 2013102923/15 dated May 8, 2015, English translation included.
International Preliminary Report on Patentability for related patent Application No. PCT/US2014/031364, dated Sep. 29, 2016.

* cited by examiner

SYNTHETIC NORIBOGAINE

CROSS REFERENCE TO RELATED APPLICATIONS

This application is a continuation application of U.S. patent application Ser. No. 13/593,454 (filed Aug. 23, 2012), which claims the benefit under 35 U.S.C. §119(e) of U.S. Provisional application No. 61/528,070, filed Aug. 26, 2011, all of which are incorporated by reference in their entirety into this application.

FIELD OF THE INVENTION

This invention relates to synthetic noribogaine free of ibogaine, methods of preparing such noribogaine, and pharmaceutically acceptable composition including such noribogaine.

STATE OF THE ART

Noribogaine is a well known compound and is a derivative of ibogaine and is sometimes referred to as 12-hydroxyibogamine. U.S. Pat. No. 2,813,873 claims noribogaine albeit as "12-O-demethylibogaine" while providing an incorrect structural formula for ibogaine. The structure of noribogaine has now been determined and found to combine the features of tyrptamine, tetrahydrohavaine and indolazepines. Noribogaine can be depicted by the following formula:

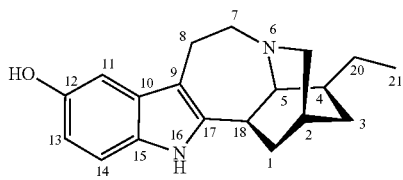

where the configuration at the 2, 4, 5, 6 and 18 atoms are 2(R), 4(S), 5(S), 6(S) and 18(R).

Noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737). Both of these patents are incorporated herein by reference in their entirety.

Noribogaine is prepared by O-demethylation of naturally occurring ibogaine:

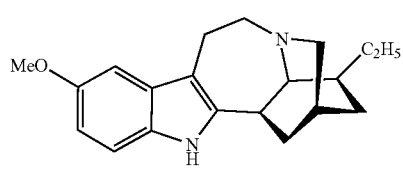

which is isolated from *Tabernanthe iboga*, a shrub of West Africa. Demethylation may be accomplished by techniques such as by reaction with boron tribromide/methylene chloride at room temperature followed by purification. Alternatively, reaction with acetic acid and hydrogen bromide can be used. Regardless, noribogaine thus prepared will contain residual ibogaine resulting from decarboxylation but incomplete O-demethylation.

Still further, noribogaine is prepared by decarboxylation and O-demethylation of naturally occurring voacangine:

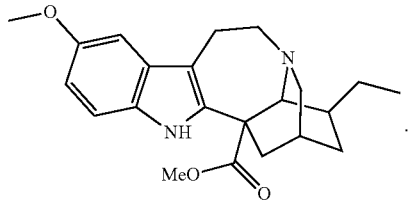 [SMILES: CCC1CC2CN3CCc4c([nH]c5ccc(OC)cc45)C(C(=O)OC)(C2)C13]

Again, noribogaine thus prepared will contain residual ibogaine resulting from decarboxylation but incomplete O-demethylation. As both ibogaine and voacangine are obtained from plants, the natural supply of ibogaine and voacangine is limited and unpredictable.

Ibogaine is known to possess hallucinogenic properties and is a Schedule 1-controlled substance in the U.S.A. Accordingly, methods for preparing noribogaine, a non-hallucinogenic and non-controlled substance, from ibogaine require high levels of assurance that contamination with unacceptable amounts of ibogaine is avoided. However, noribogaine prepared by demethylation has not been reported as being substantially free of ibogaine (e.g., not more than 0.5 wt % relative to noribogaine). At best, U.S. Pat. No. 6,348,456 claims an essentially pure noribogaine compound but fails to disclose any methods for purification let alone what the phrase "essentially pure" encompassed or, for that matter, the level of ibogaine remaining in the composition. The synthesis of noribogaine from ibogaine was reported in U.S. Pat. No. 2,813,873. However, the '873 patent is also silent as to the purity of the noribogaine obtained in that synthetic process. Overall, it is accurate to state that the use of ibogaine or voacangine as a starting material for preparing noribogaine is complicated by the presence of residual ibogaine in the noribogaine thus prepared.

Accordingly, there is an ongoing need to provide synthetic noribogaine prepared in a manner in which ibogaine or voacangine is not an intermediate or side product, and which preferably provides noribogaine in an enantiomerically enriched (with more of the 2(R), 4(S), 5(S), 6(S) and 18(R) enantiomer) form.

SUMMARY OF THE INVENTION

In one aspect, this invention provides synthetic noribogaine. Preferably, the synthetic noribogaine is free of ibogaine. More preferably, the synthetic noribogaine is also free of other naturally occurring *Tabernanth iboga* alkaloids. In one embodiment, at least 95% of the synthetic noribogaine is present as the 2(R), 4(S), 5(S), 6(S) and 18(R) enantiomer. In another embodiment, the synthetic noribogaine contains less than 1 ppt $C^{14}$. Preferably, the synthetic noribogaine contains less than 0.95 ppt, and still more preferably, less than 0.8 ppt $C^{14}$. In another aspect, this invention provides a pharmaceutical composition comprising the synthetic noribogaine provided herein and a pharmaceutically acceptable excipient. In another aspect, this invention provides methods for preparing the synthetic noribogaine free of ibogaine, and optionally free of other naturally occurring *Tabernanth iboga* alkaloids. In another aspect, this invention provides novel compounds useful in the synthesis of the synthetic noribogaine provided according to this invention.

DETAILED DESCRIPTION OF THE INVENTION

This invention is directed to synthetic noribogaine and compositions comprising highly pure noribogaine, preferably, as the 2(R), 4(S), 5(S), 6(S) and 18(R) enantiomer. However, prior to describing this invention in greater detail, the following terms will first be defined.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

It must be noted that as used herein and in the appended claims, the singular forms "a", "an", and "the" include plural referents unless the context clearly dictates otherwise. Thus, for example, reference to "a pharmaceutically acceptable excipient" includes a plurality of such excipients.

DEFINITIONS

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, the term "noribogaine" refers to the alkaloid noribogaine including all enantiomers thereof, and also includes pharmaceutically acceptable salts of each thereof. Of particular interest is the enantiomer depicted by the formula:

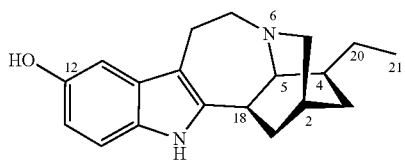

where the configuration at the 2, 4, 5, 6 and 18 atoms are 2(R), 4(S), 5(S), 6(S) and 18(R).

As used herein, the term "noribogaine free of ibogaine" refers to noribogaine that contains less than 0.5 wt %, less than 0.1 wt %, less than 0.05 wt %, preferably, less than 0.02 wt % (or 200 ppm), more preferably, less than 100 ppm, or still more preferably less than 50 ppm ibogaine relative to the total amount of noribogaine. In one embodiment, the noribogaine contains no ibogaine detectable by known methods to detect ibogaine or such a compound. In a particularly preferred embodiment, the noribogaine is synthetic noribogaine which does not encompass ibogaine as an intermediate and, accordingly, is free of ibogaine.

As used herein, the term "other naturally occurring *Tabernanth iboga* alkaloids" refer to the following alkaloids: tabernanthine, ibogamine, ibogaline, iboluteine, iboquine, desmethoxyiboluteine, and hydroxyindolenine derivatives of ibogaine, ibogamine, voacangine, gabonine, kisanthine, and kimvuline. These alkaloids are, in addition to ibogaine, isolated from the *Tabernanth iboga* plant.

As used herein, the term "noribogaine free of one or more of other naturally occurring *Tabernanth iboga* alkaloids" refer to noribogaine that contains less than 1 wt %, less than 0.5 wt %, preferably, less than 0.1 wt %, or still more preferably, less than 0.02 wt % of one or more of the other naturally occurring *Tabernanth iboga* alkaloids, relative to the total amount of noribogaine. In a preferred embodiment, the noribogaine is synthetic noribogaine which does not encompass any of these alkaloids as an intermediate and, accordingly, is free of ibogaine.

As used herein, "alkyl" refers to groups having from 1 to 6 carbon atoms and more preferably 1 to 3 carbon atoms. The alkyl group may contain linear or branched carbon chains. This term is exemplified by groups such as methyl, ethyl, n-propyl, iso-propyl, n-butyl, t-butyl, n-pentyl and the like. The term "$C_x$ alkyl" refers to an alkyl group having x carbon atoms, wherein x is an integer, for example, $C_3$ refers to an alkyl group having 3 carbon atoms.

As used herein, "alkoxy" refers to —O-alkyl.

As used herein, the term "reaction conditions" refers to details under which a chemical reaction proceeds. Examples of reaction conditions include, but are not limited to, one or more of following: reaction temperature, solvent, pH, pressure, reaction time, mole ratio of reactants, the presence of a base or acid, or catalyst, etc.

As used herein, the term "pharmaceutically acceptable excipient" refers to a non toxic excipient useful for administration to a patient, such as, human.

As used herein, the term "pharmaceutically acceptable salt" refers to pharmaceutically acceptable, non toxic, salts derived from a variety of organic and inorganic counter ions well known in the art and include, by way of example only, when the molecule contains an acidic functionality, counter ions such as sodium, potassium, calcium, magnesium, ammonium, tetraalkyl ammonium, and the like, and when the molecule contains a basic functionality, counter ions such as chloride, bromide, tartrate, mesylate, acetate, maleate, oxalate and the like.

As used herein, the term "protecting group" or "Pg" refers to well known functional groups which, when bound to a functional group, render the resulting protected functional group inert to the reaction conditions to be conducted on other portions of the compound and which, at the appropriate time, can be reacted to regenerate the original functionality under deprotection conditions. The identity of the protecting group is not critical and is selected to be compatible with the remainder of the molecule. In one embodiment, the protecting group is an "amino protecting group" which protects the amino functionality of noribogaine intermediates during the noribogaine synthesis described herein. Examples of amino protecting groups include, for instance, benzyl, acetyl, oxyacetyl, carbonyloxybenzyl (Cbz), and the like. In another embodiment, the protecting group is a "hydroxy protecting group" which protects the hydroxyl functionality of noribogaine intermediates during the noribogaine synthesis described herein. Examples of hydroxyl protecting groups include, for instance, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, and benzyl. Additional examples of hydroxy protecting groups may be found in standard reference works such as Greene and Wuts, Protective Groups in Organic Synthesis., 2d Ed., 1991, John Wiley & Sons, and McOmie Protective Groups in Organic Chemistry, 1975, Plenum Press. Methods for protecting and deprotecting the phenolic hydroxyl group of the compounds disclosed herein can be found in the art, and specifically in Greene and Wuts, supra, and the references cited therein.

Synthetic Noribogaine and Intermediates Thereto

Synthetic noribogaine provided according to this invention is prepared as shown in the non limiting illustration below.

Compound 6 is converted to intermediate 17 as shown below:

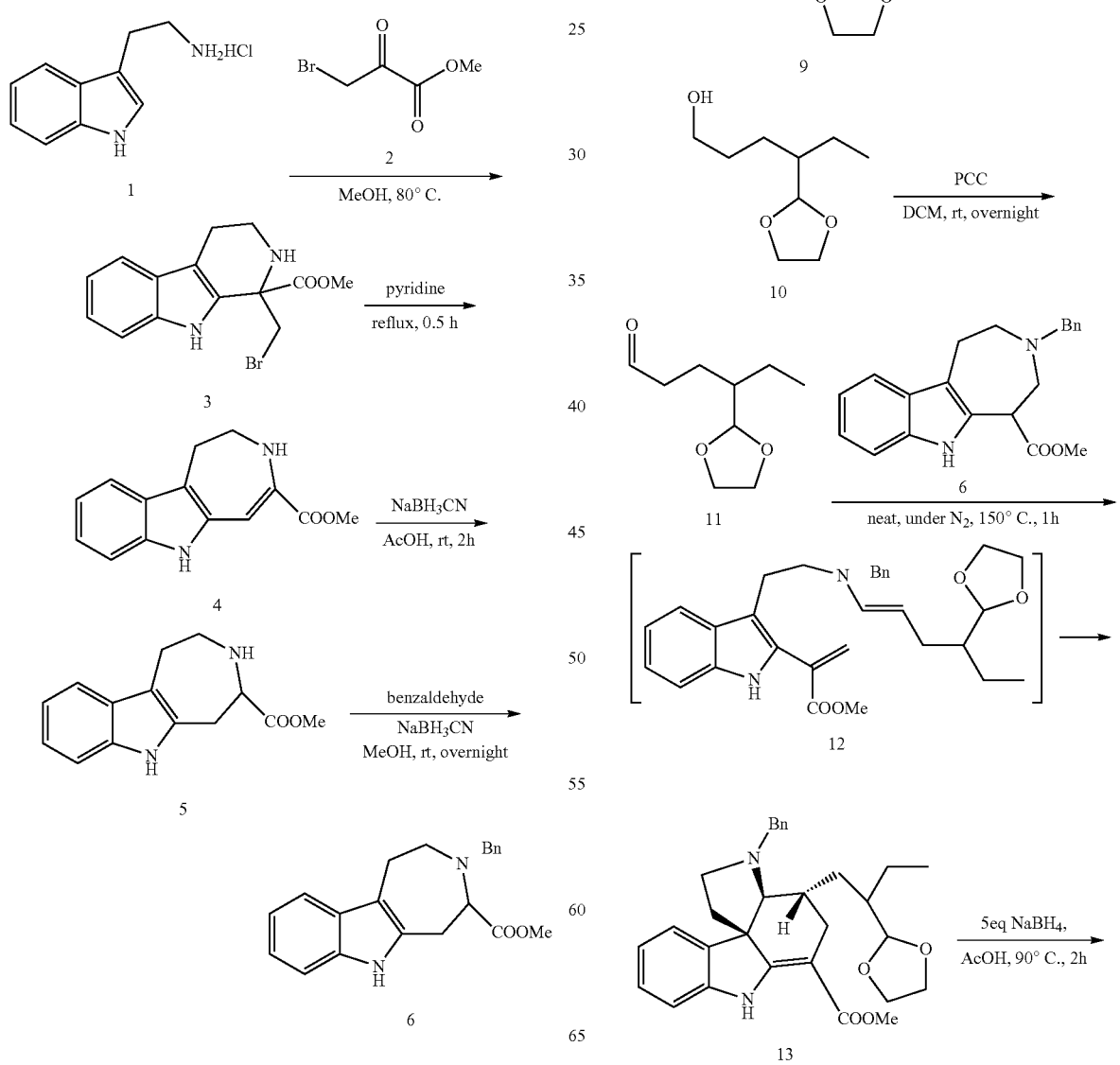

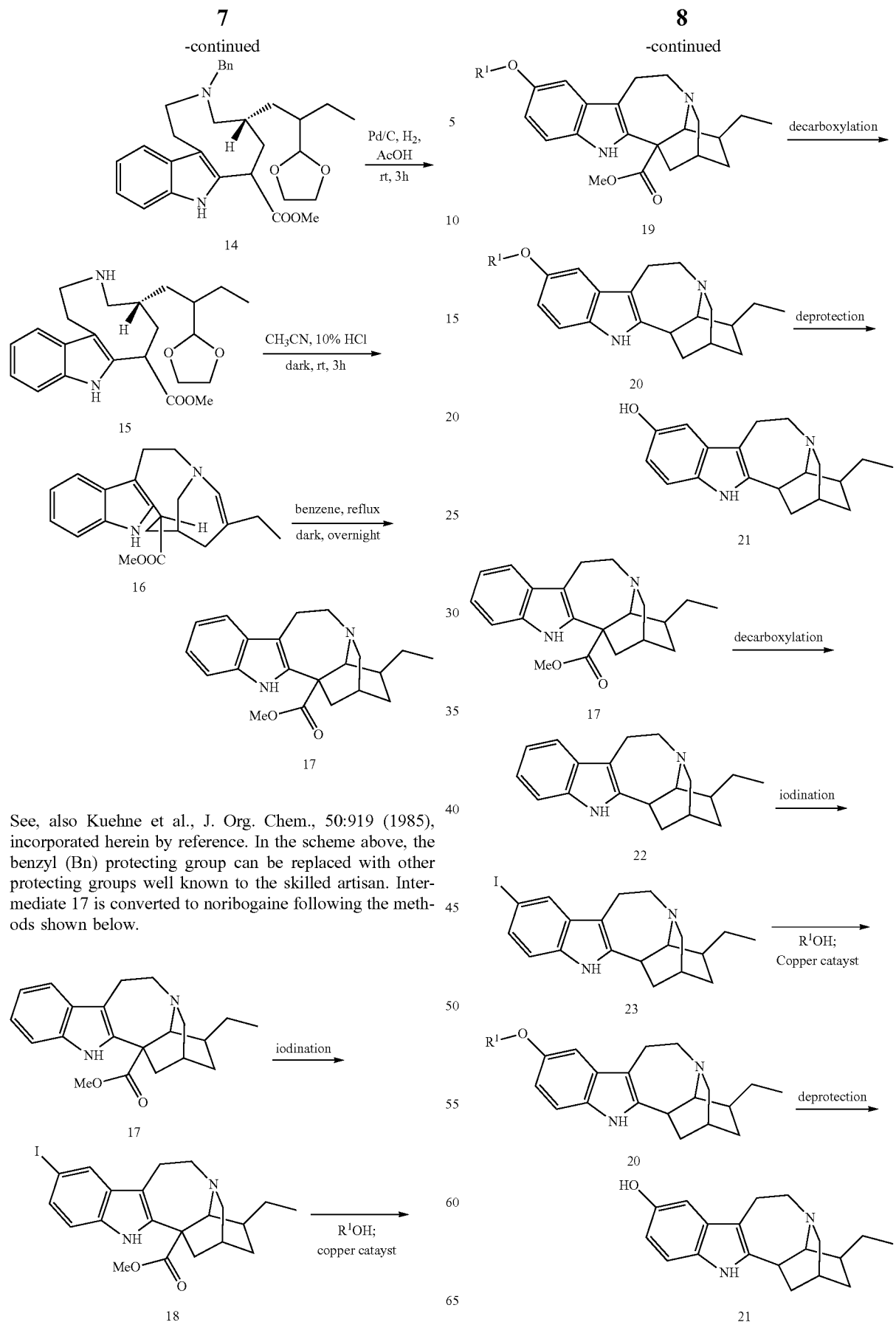
See, also Kuehne et al., J. Org. Chem., 50:919 (1985), incorporated herein by reference. In the scheme above, the benzyl (Bn) protecting group can be replaced with other protecting groups well known to the skilled artisan. Intermediate 17 is converted to noribogaine following the methods shown below.

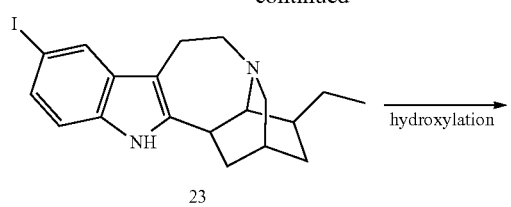

23

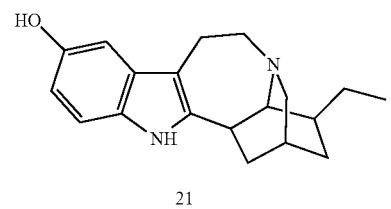

21

The decarboxylation is performed following various methods well known to the skilled artisan, such as using refluxing hydrazine. The decarboxylation is also contemplated to be performed by hydrolyzing the —COOMe group to an acid, and reacting the corresponding sodium or lithium salt with aqueous mineral acid.

With tryptamine (compound 1) used as a starting material, the hydroxy group is incorporated at the 5-position of the indole ring (the 12-position of noribogaine) via an iodo or bromo substituted indole intermediate (such as compounds 18 and 23). The iodo group is conveniently incorporated into the indole ring by reacting compound 17 or 22, e.g. and without limitation, with N-iodosuccinimide (NIS). The iodo group is also incorporated using a phenyl iodonium intermediate, and displacing the phenyl group as schematically shown below. The iodo or the bromo group is also incorporated by nitration, reducing the nitro group to an amino group, diazotizing the amino group, and reacting the diazonium compound with CuI or CuBr. Alternatively, the diazonium compound is converted to a hydroxy group simply by reacting with water. These transformations are illustrated below.

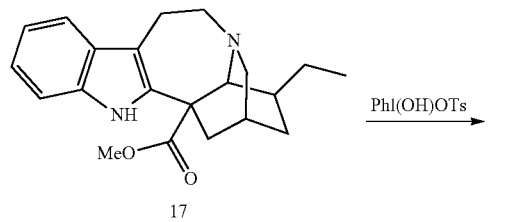

17

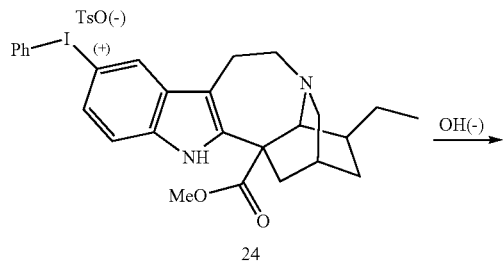

24

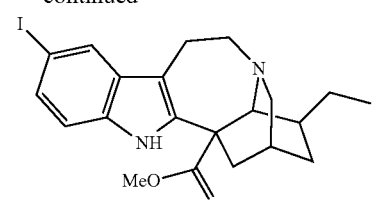

18

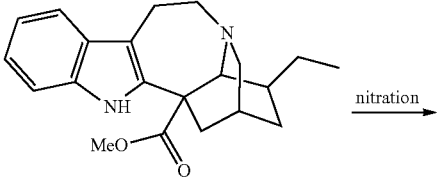

17

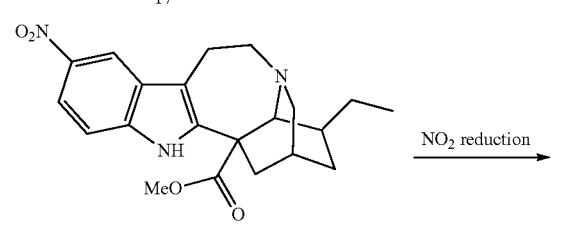

25

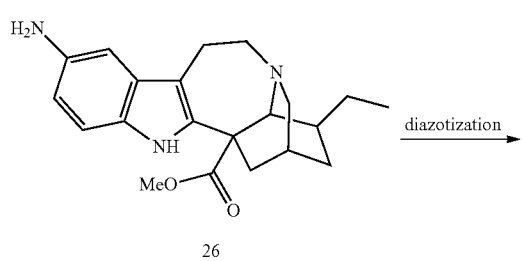

26

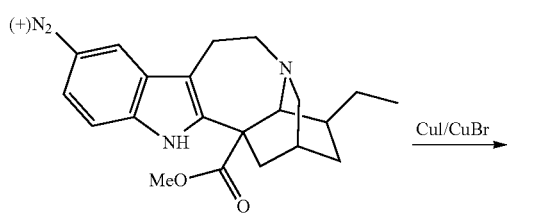

27

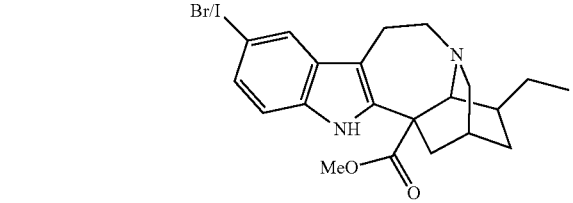

18 or 28

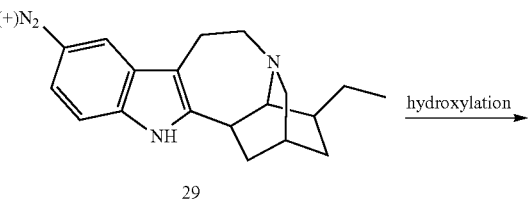

29

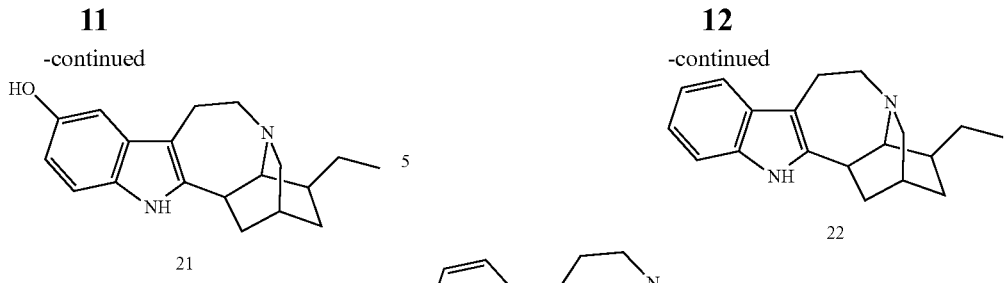

21

Compound 22 can be iodinated, brominated, or hydroxylated at the 12-position, in similar manner.

The iodo group is converted to —OR' by reacting with the corresponding $R^1OH$ or $R^1O(-)$, e.g., in presence of a copper catalyst. For example, $R^1$ is any hydroxy protecting group other than methyl. In one embodiment, —OR' is benzyloxy (~OBn) or a substituted benzyloxy group. As used herein, substituted benzyloxy refers to:

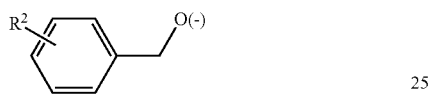

wherein $R^2$ is $C_1$-$C_6$ alkyl or $C_1$-$C_6$ alkoxy. For example, and without limitation, CuI and a ligand such as tetramethyl phenanthroline (see, for example, "An Improved Cu-Based Catalyst System for the Reactions of Alcohols with Aryl Halides", Altman et al., *J. Org. Chem.*, 2008, 73, 284-286, incorporated herein by reference), or CuBr (U.S. Pat. No. 4,422,955, incorporated herein by reference) are useful for incorporating an —$OR^1$ group, such as, benzyloxy or substituted benzyloxy group.

According to this invention, compound 17 is also converted to noribogaine via the route shown below. The alcohol, compound 30, provides a convenient route to the desired enantiomer, compound 30A (which yields substantially 2(R), 4(S), 5(S), 6(S) and 18(R) noribogaine), in a substantially pure form. For this purpose, compound 30 is esterified with a chiral carboxylic acid (such as R*COOH) and diastereomeric forms of compound 31 are separated. Various such chiral carboxylic acids are well known to the skilled artisan. The hydroxymethyl group is removed from compound 30 or 30A following a retro aldol reaction.

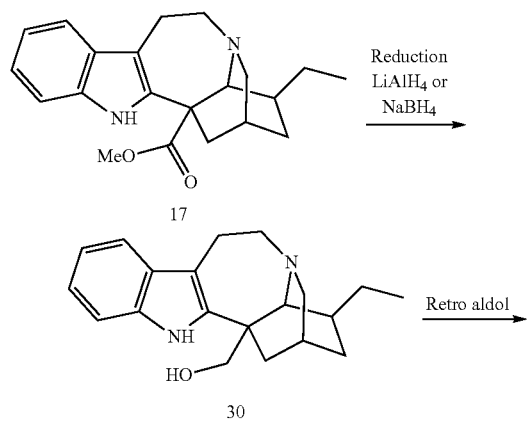

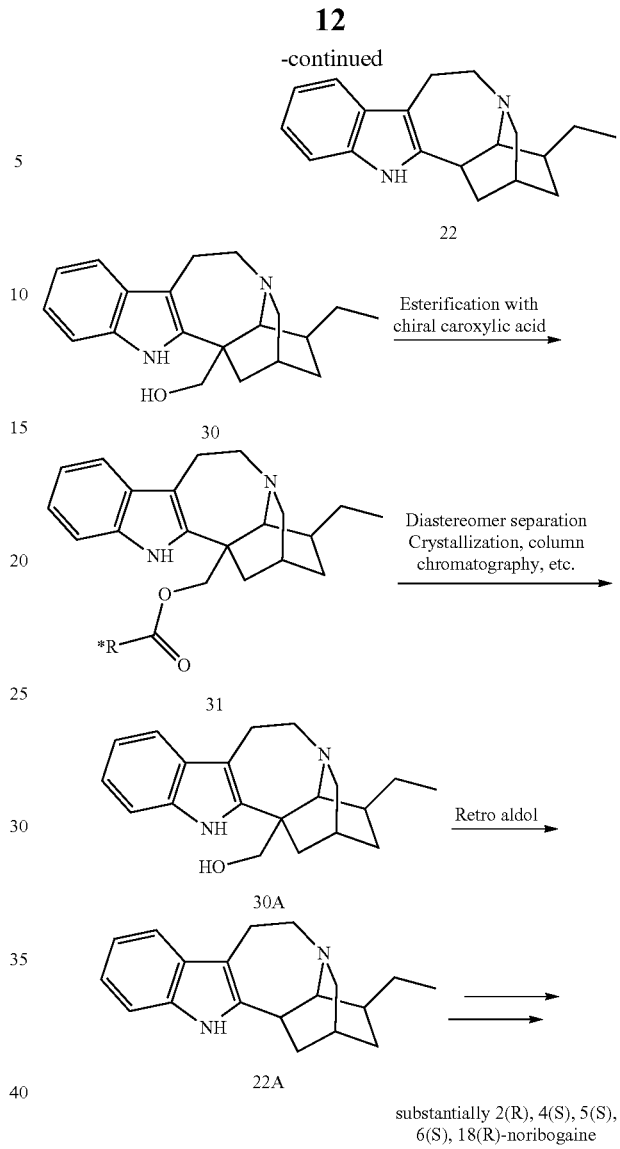

Thus in one embodiment, this invention provides a method comprising contacting a compound of formula 17 with an iodinating agent under reaction conditions to provide the compound of formula 18. In another embodiment, the method further comprises, contacting the compound of formula 18 with a benzyloxy ((-)OBn) or substituted benzyloxy anion in presence of copper catalyst under reaction conditions to provide a compound of formula 19. In another embodiment, the method further comprises decarboxylating the compound of formula 19 to provide the compound of formula 20.

In another embodiment, this invention provides a method comprising contacting a compound of formula 22 with an iodinating agent under reaction conditions to provide the compound of formula 23. In another embodiment, the method further comprises contacting the compound of formula 23 with a benzyloxy ((-)OBn) or substituted benzyloxy anion in presence of copper catalyst to provide a compound of formula 20. In another embodiment, the method further comprises removing the benzyl or substituted benzyl protecting group under conditions to provide noribogaine. Conditions suitable for removing a benzyl or a substituted benzyl protecting group include, without limitation, hydrogenolysis using hydrogen and a Pd, Pt, or Rh or their oxide based catalyst.

In another embodiment, this invention provides a method comprising contacting the compound of formula 23 with hydroxide and a copper catalyst under conditions to provide noribogaine.

It is also contemplated that synthetic noribogaine provided according to this invention is prepared starting from a halogenated tryptamine.

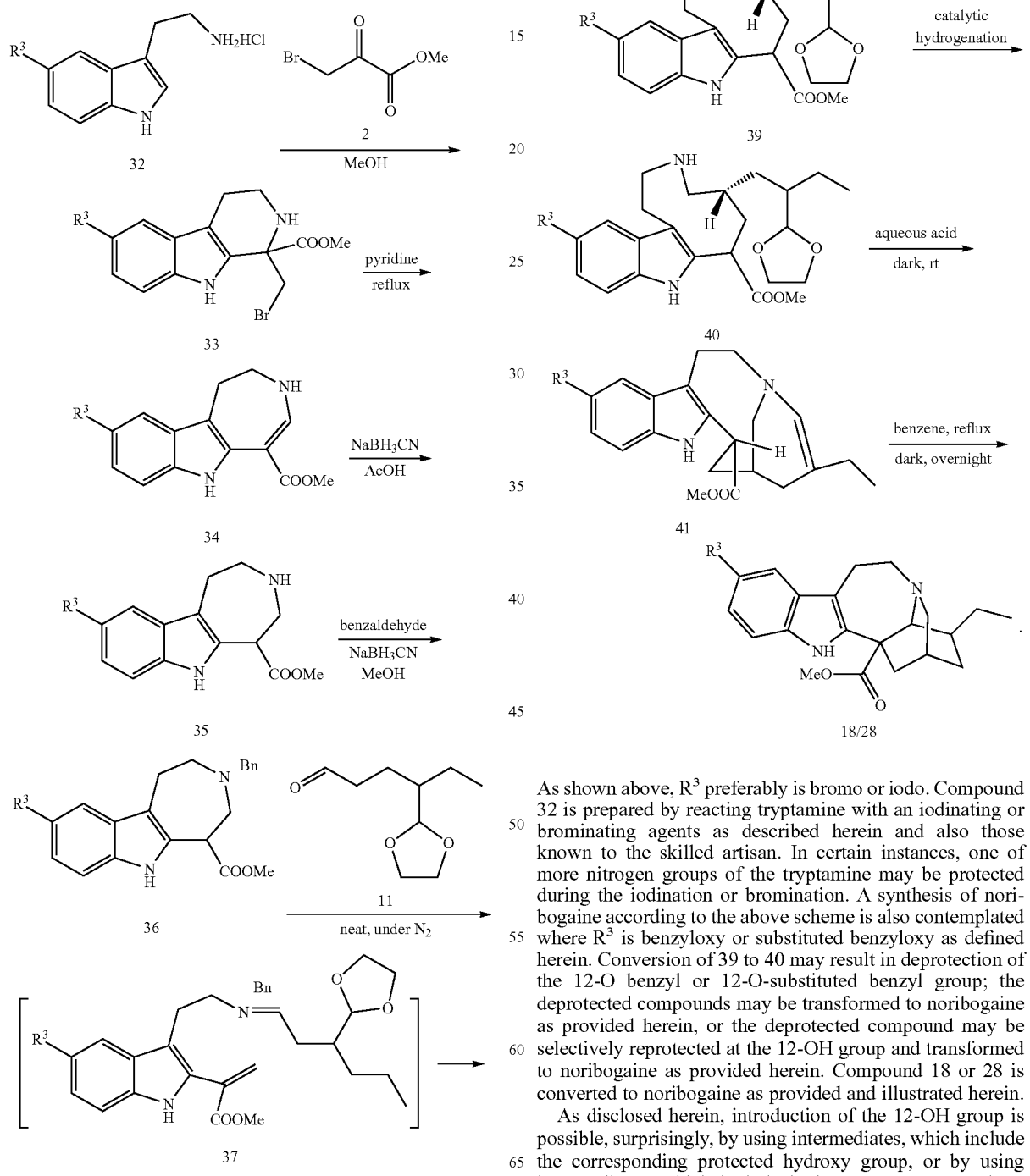

As shown above, $R^3$ preferably is bromo or iodo. Compound 32 is prepared by reacting tryptamine with an iodinating or brominating agents as described herein and also those known to the skilled artisan. In certain instances, one of more nitrogen groups of the tryptamine may be protected during the iodination or bromination. A synthesis of noribogaine according to the above scheme is also contemplated where $R^3$ is benzyloxy or substituted benzyloxy as defined herein. Conversion of 39 to 40 may result in deprotection of the 12-O benzyl or 12-O-substituted benzyl group; the deprotected compounds may be transformed to noribogaine as provided herein, or the deprotected compound may be selectively reprotected at the 12-OH group and transformed to noribogaine as provided herein. Compound 18 or 28 is converted to noribogaine as provided and illustrated herein.

As disclosed herein, introduction of the 12-OH group is possible, surprisingly, by using intermediates, which include the corresponding protected hydroxy group, or by using intermediates, which include hydroxy precursors such as halo, nitro, amino, and the like.

As will be apparent to the skilled artisan, the methods of making synthetic noribogaine as provided herein also require routine steps of separation and purification, which are performed by column chromatography, crystallization, and the like, as also well known to the skilled artisan. Enatiomerically enriched synthetic noribogaine, or an enatiomerically enriched intermediate thereto as utilized and provided herein is contemplated to be obtained, inter alia, by chiral chromatographic separation, and/or resolution via diastereomeric salt formation, and/or separation of diastereomeric derivatives. Chiral acids and bases suitable for resolving synthetic noribogaine or an intermediate thereto will be well known to the skilled artisan.

The synthetic ibogaine prepared herein is free of ibogaine, and optionally, one or more of the other naturally occurring *Tabernanth iboga* alkaloids, because, e.g., such alkaloids, particularly those that are methoxylated on the indole ring, including ibogaine are not intermediates and/or by-products in the preparation of noribogaine according to this invention. Ibogaine or the one or more of other naturally occurring *Tabernanth iboga* alkaloids are present in ibogaine, obtained from natural sources by partial synthesis, as an impurity.

The synthetic noribogaine of this invention is distinguished from plant derived noribogaine (e.g., and without limitation, noribogaine synthesized from naturally occurring ibogaine or voacangine) by its $^{14}C$ content. $^{14}C$ has a half-life of about 5,730 years and is generated in the upper atmosphere as $^{14}CO_2$. The amount of $^{14}CO_2$ present is approximately 1 ppt (parts per trillion) and, through photosynthesis, accumulates in plants resulting in a $^{14}C$ content of plant material of approximately 1 ppt. Accordingly, plant derived noribogaine (e.g., and without limitation, noribogaine synthesized from naturally occurring ibogaine or voacangine) is expected to have approximately 1 ppt $^{14}C$. Conversely, the noribogaine and intermediates disclosed herein are derived from fossil fuels, which, due to $^{14}C$ decay, would have a $^{14}C$ content of less than 1 ppt $^{14}C$. Accordingly, provided herein is noribogaine having a $^{14}C$ content of less than 1 ppt, preferably, less than 0.95 ppt, or more preferably less than 0.8 ppt. In one embodiment, provided herein is synthetic noribogaine having a $^{14}C$ content of less than 0.6 ppt, or less than 0.5 ppt, or less than 0.4 ppt, or less than 0.3 ppt, or less than 0.2 ppt, or less than 0.1 ppt. In another embodiment, provided herein is synthetic noribogaine having a $^{14}C$ content of 0.8 ppt to 0.95 ppt or 0.7 ppt to 0.95 ppt. The amount of $^{14}C$ can be analyzed using methods well known in the art (i.e. radiocarbon analyses can be carried out according to the American Society for Testing Materials ASTM D6866 procedure (ASTM international, 100 Barr Harbon Drive, PO Box C700, West Conshohocken, Pa. 19428-2959)). Furthermore, provided is a method for distinguishing synthetic noribogaine from plant derived noribogaine based on the $^{14}C$ content.

In another aspect, this invention provides the following compounds:

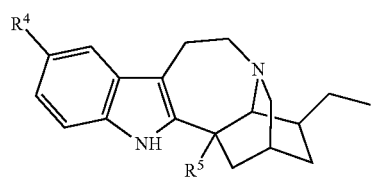

I

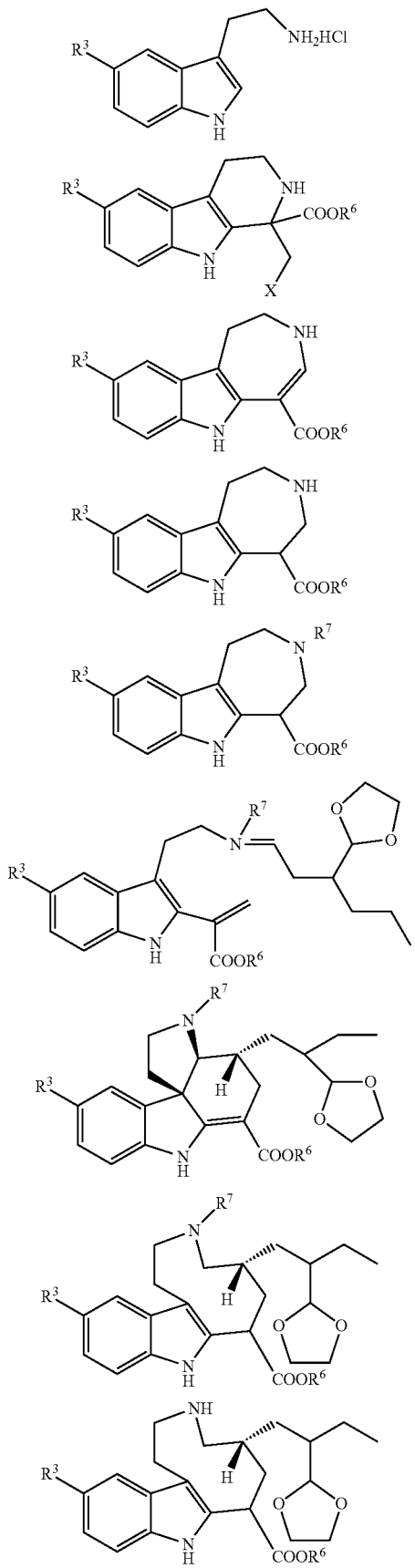

-continued

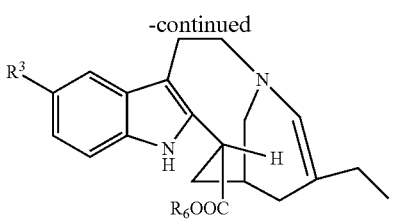

wherein,
X is chloro, bromo, or iodo;
$R^4$ is H, $NO_2$, $NH_2$, $-N_2(+)$, $-OR^1$, or $R^3$;
$R^1$ is a hydroxy protecting group other than methyl;
$R^3$ is iodo, bromo, benzyloxy, substituted benzyloxy, allyloxy, or trialkylsilyloxy;
$R^5$ is H, $CO_2R^6$, $-CH_2OH$, or $-CH_2O_2CR^*$;
provided that, when $R^5$ is H, then $R^4$ is not H; and
provided that when $R^4$ is H, then $R^5$ is $-CH_2O_2CR^*$;
$R^*$ is an asymmetric carbon atom such that $RCO_2H$ is a chiral carboxylic acid;
$R^6$ is H or $C_1$-$C_6$ alkyl; and
$R^7$ is an amino protecting group;
or a salt, preferably a pharmaceutically acceptable salt, thereof.

In one embodiment, $R^4$ is H. In another embodiment, $R^4$ is $NO_2$. In another embodiment, $R^4$ is $NH_2$. In another embodiment, $R^4$ is $-N_2(+)$. In another embodiment, $R^4$ is $-OR^1$. In another embodiment, $R^1$ is benzyl. In another embodiment, $R^1$ is:

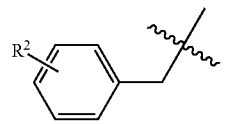

and $R^2$ is $C_1$-$C_6$ alkyl or $C_1$-$C_6$ alkoxy. In another embodiment, $R^4$ is $R^3$. In another embodiment, $R^3$ is iodo. In another embodiment, $R^3$ is bromo. In another embodiment, $R^3$ is benzyloxy. In another embodiment, $R^3$ is substituted benzyloxy.

In another embodiment, $R^5$ is H. In another embodiment, $R^5$ is $-CO_2Me$. In another embodiment, $R^5$ is $-CH_2O_2CR^*$. In another embodiment, $R^5$ is $-CH_2OH$.

In another embodiment, X is chloro. In another embodiment, X is bromo. In another embodiment, X is iodo.

In another embodiment, $R^7$ is benzyl.

In another aspect, this invention provides synthetic noribogaine having 2(R), 4(S), 5(S), 6(S) and 18(R), configuration (the naturally occurring configuration); noribogaine having 2(S), 4(R), 5(R), 6(R) and 18(S) configuration; or a salt, preferably a pharmaceutically acceptable salt thereof.

In another aspect, this invention provides a compound of formula:

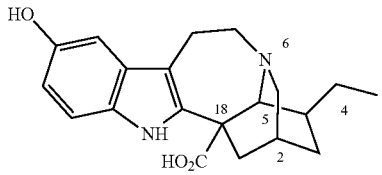

or a salt, preferably a pharmaceutically acceptable salt, thereof; or
an enantiomer or diastereomer of each thereof.

In one embodiment, the compound is a pure or substantially pure enantiomer having configurations at the 2, 4, 5, 6, and 18 position which are the same as that in naturally occurring voacangine. In another embodiment, the compound is a pure or substantially pure enantiomer having configurations at the 2, 4, 5, 6, and 18 positions, which are the mirror images of that in naturally occurring voacangine.

In another aspect, this invention provides a compound of formula:

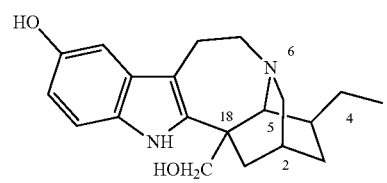

or a salt, preferably a pharmaceutically acceptable salt, thereof; or
an enantiomer or diastereomer of each thereof.

In certain embodiments, the compounds provided by this invention are provided in substantially enatiomerically enriched or diastereomerically enriched form.

The various compounds provided herein are prepared according to methods disclosed here and/or those known to the skilled artisan.

UTILITY

2(R), 4(S), 5(S), 6(S) and 18(R) noribogaine has utility in treating drug dependency and as an analgesic. See U.S. Pat. No. 6,348,456 7,220,737, supra. The novel compounds provided herein have utility as intermediates to synthetic noribogaine or as compounds having activity in drug dependency or as analgesics.

It will be apparent to the skilled artisan that the products synthesized according to this invention are separated, as required, by techniques well known to the skilled artisan, such as, column chromatographic separation and crystallization.

The invention claimed is:
1. A pharmaceutically acceptable composition comprising:
a compound of Formula I:

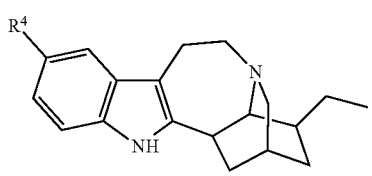

or a salt thereof wherein,
$R^4$ is —O-PG, OMs, or OTs;
PG is selected from the group consisting of:
a) —($C_1$-$C_6$ alkyl)-X where X is selected from the group consisting of $C_6$-$C_{10}$ aryl, $C_2$-$C_{10}$ heteroaryl, and $CO_2H$ or an ester thereof; and b)

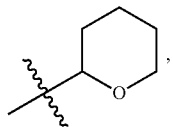,

—CH$_2$CH=CH$_2$, —CH$_2$OCH$_3$, —CHO, and —Si(R$^{21}$)$_3$ where each R$^{21}$ is selected from the group consisting of C$_6$-C$_{10}$ aryl, and C$_2$-C$_{10}$ heteroaryl, and a pharmaceutically acceptable excipient.

2. The pharmaceutically acceptable composition of claim 1 wherein,

R$^4$ is selected from the group consisting of: OBn, OMs, OTs, and OCH$_2$CH=CH$_2$.

3. The pharmaceutically acceptable composition of claim 1, which is free of ibogaine.

4. A pharmaceutically acceptable composition comprising:

a compound of Formula I:

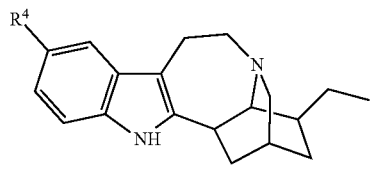

I or a salt thereof wherein,

R$^4$ is —O-(C$_1$-C$_6$ alkyl)-X, where X is selected from the group consisting of C$_6$-C$_{10}$ aryl, C$_2$-C$_{10}$ heteroaryl, and CO$_2$H or an ester thereof; and a pharmaceutically acceptable excipient.

5. The pharmaceutically acceptable composition of claim 4, wherein X is C$_6$-C$_{10}$ aryl.

6. The pharmaceutically acceptable composition of claim 4, wherein X is C$_2$-C$_{10}$ heteroaryl.

7. The pharmaceutically acceptable composition of claim 4, wherein X is CO$_2$H or an ester thereof.

8. The pharmaceutically acceptable composition of claim 4, which is free of ibogaine.

9. A pharmaceutically acceptable composition comprising:

a compound of Formula I:

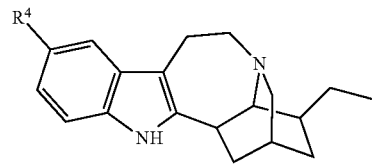

I or a salt thereof wherein,

R$^4$ is —O-PG,

PG is selected from the group consisting of:

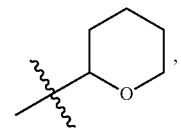 [SMILES: *C1CCCCO1],

—CH$_2$CH=CH$_2$, —CH$_2$OCH$_3$, and —CHO;

and a pharmaceutically acceptable excipient.

10. The pharmaceutically acceptable composition of claim 9, which is free of ibogaine.

* * * * *